US007405278B2

(12) United States Patent
Shibuya

(10) Patent No.: US 7,405,278 B2
(45) Date of Patent: Jul. 29, 2008

(54) CHIMERIC HUMAN-TYPE VASCULAR ENDOTHELIAL CELL GROWTH FACTOR

(76) Inventor: Masabumi Shibuya, 5374-18-601 Shiba, Kawaguchi-shi, Saitama 333-0866 (JP)

( * ) Notice: Subject to any disclaimer, the term of this patent is extended or adjusted under 35 U.S.C. 154(b) by 791 days.

(21) Appl. No.: 10/343,825

(22) PCT Filed: Aug. 9, 2001

(86) PCT No.: PCT/JP01/06856

§ 371 (c)(1),
(2), (4) Date: Sep. 9, 2003

(87) PCT Pub. No.: WO02/14367

PCT Pub. Date: Feb. 21, 2002

(65) Prior Publication Data

US 2004/0038341 A1 Feb. 26, 2004

(30) Foreign Application Priority Data

Aug. 10, 2000 (JP) ............................ 2000-242629

(51) Int. Cl.
*C07K 14/475* (2006.01)

(52) U.S. Cl. ...................................... 530/399; 530/350

(58) Field of Classification Search ....................... None
See application file for complete search history.

(56) References Cited

U.S. PATENT DOCUMENTS

| | | | | |
|---|---|---|---|---|
| 5,994,300 | A | 11/1999 | Bayne et al. | |
| 6,140,073 | A | 10/2000 | Bayne et al. | |
| 6,569,434 | B1 | 5/2003 | Bayne et al. | |
| 2005/0267024 | A1 * | 12/2005 | Alitalo et al. | 514/12 |

FOREIGN PATENT DOCUMENTS

WO 98/49300 11/1998

OTHER PUBLICATIONS

Napoleone Ferrara et al., "The Biology of Vascular Endothelial Growth Factor", Endocrine Reviews, vol. 18, No. 1, pp. 4-25 (1997).

Masabumi Shibuya, "Role of VEGF-FLT Receptor System in Normal and Tumor Angiogenesis", Advances in Cancer Research, vol. 67, pp. 281-316 (1995).

M. Shibuya et al., "Structure and Function of Vascular Endothelial Growth Factor Receptor-1 and -2", Current Topics in Microbiology and Immunology, vol. 237, pp. 59-83 (1999).

Tomoko Takahashi et al., "VEGF Activates Protein Kinase C-Dependent, but Ras-Independent Raf-MEK-MAP Kinase Pathway for DNA Synthesis in Primary Endothelial Cells", Oncogene, vol. 18, pp. 2221-2230 (1999).

Bernhard Barleon et al., "Migration of Human Monocytes in Response to Vascular Endothelial Growth Factor (VEGF) is Mediated Via the VEGF Receptor flt-1", Blood, vol. 87, No. 8, pp. 3336-3343 (1996).

Sachiyo Ogawa et al., "A Novel Type of Vascular Endothelial Growth Factor, VEGF-E (NZ-7 VEGF), Preferentially Utilizes KDR/Flk-1 Receptor and Carries a Potent Mitotic Activity without Heparin-binding Domain", The Journal of Biological Chemistry, vol. 273, No. 47, pp. 31273-31282 (1998).

David J. Lyttle et al., "Homologs of Vascular Endothelial Growth Factor are Encoded by the Poxvirus Orf Virus", Journal of Virology, vol. 68, No. 1, pp. 84-92 (1994).

Marlene Meyer et al., "A Novel Endothelial Growth Factor Encoded by Orf Virus, VEGF-E, Mediates Angiogenesis Via Signalling Through VEGFR-2 (KDR) but not BEGFR-1 (Flt-1) Receptor Tyrosine Kinases", The EMBO Journal, vol. 18, No. 2, pp. 363-374 (1999).

Nader Rahimi et al., "Receptor Chimeras Indicate that the Vascular Endothelial Growth Factor Receptor-1 (VEGFR-1) Modulates Mitogenic Activity of VEGFR-2 in Endothelial Cells", The Journal of Biological Chemistry, vol. 275, No. 22, pp. 16986-16992 (2000).

M. Clauss et al., "Vascular Permeability Factor: A Tumor-Derived Polypeptide that Induces Endothelial Cell and monocyte Procoagulant Activity, and Promotes Monocyte Migration", J. Exp. Med., vol. 172, pp. 1535-1545 (1990).

* cited by examiner

*Primary Examiner*—Marianne P Allen
(74) *Attorney, Agent, or Firm*—Greenblum & Bernstein, P.L.C.

(57) ABSTRACT

An object of the present invention is to provide a chimera VEGF-E having a reduced antigenicity while maintaining the activity of VEGF-E. The present invention provides a chimera protein having an activity of growing vascular endothelial cells, which is obtained by substituting a part of the sequence of a VEGF analogous protein having an activity of vascularization that binds to KDR (VEGF receptor-2) but does not bind to Flt-1 (VEGF receptor-1) with a corresponding sequence of a human-derived VEGF analogous protein.

2 Claims, 17 Drawing Sheets

Preparation of VEGF-$E_{NZ7}$ chimera protein; Coomassie stainning

Experiment for competitive inhibition of VEGF-$E_{NZ7}$ chimera protein on the KDR receptor Experiment of the autophosphorylation of KDR receptor

Fig.7

```
                9                  18                 27                 36                 45                 54
5'  ATG AAG TTA ACA GCT ACG TTA CAA GTT GTT GTT GCA TTG TTA ATA TGT ATG TAT
    --- --- --- --- --- --- --- --- --- --- --- --- --- --- --- --- --- ---
     M   K   L   T   A   T   L   Q   V   V   V   A   L   L   I   C   M   Y

                63                 72                 81                 90                 99                108
    AAT TTG CCA GAA TGC GTG TCT CAG AGT AAT GAT TCA CCT CCT TCA ACC AAT GAC
    --- --- --- --- --- --- --- --- --- --- --- --- --- --- --- --- --- ---
     N   L   P   E   C   V   S   Q   S   N   D   S   P   P   S   T   N   D

               117                126                135                144                153                162
    TGG ATG CGT ACA CTA GAC AAA AGT GGT TGT AAA CCT AGA GAT ACT GTT GTT TAT
    --- --- --- --- --- --- --- --- --- --- --- --- --- --- --- --- --- ---
     W   M   R   T   L   D   K   S   G   C   K   P   R   D   T   V   V   Y

               171                180                189                198                207                216
    TTG GGA GAA GAA TAT CCA GAA AGC ACT AAC CTG CAG TAT AAT CCC CGG TGC GTA
    --- --- --- --- --- --- --- --- --- --- --- --- --- --- --- --- --- ---
     L   G   E   E   Y   P   E   S   T   N   L   Q   Y   N   P   R   C   V

               225                234                243                252                261                270
    ACT GTT AAA CGA TGC AGT GGT TGC TGT AAC GGT GAC GGT CAA ATA TGT ACA GCG
    --- --- --- --- --- --- --- --- --- --- --- --- --- --- --- --- --- ---
     T   V   K   R   C   S   G   C   C   N   G   D   G   Q   I   C   T   A

               279                288                297                306                315                324
    GTT GAA ACA AGA AAT ACA ACT GTA ACA GTT TCA GTA ACC GGC GTG TCT AGT TCG
    --- --- --- --- --- --- --- --- --- --- --- --- --- --- --- --- --- ---
     V   E   T   R   N   T   T   V   T   V   S   V   T   G   V   S   S   S

               333                342                351                360                369                378
    TCT GGT ACC AAT AGT GGT GTA TCT ACT AAC CTT CAA AGA ATA AGT GTT ACA GAA
    --- --- --- --- --- --- --- --- --- --- --- --- --- --- --- --- --- ---
     S   G   T   N   S   G   V   S   T   N   L   Q   R   I   S   V   T   E

               387                396                405                414                423                432
    CAC ACA AAG TGC GAT TGT ATT GGT AGA ACA ACG ACA ACA CCT ACG ACC ACT AGG
    --- --- --- --- --- --- --- --- --- --- --- --- --- --- --- --- --- ---
     H   T   K   C   D   C   I   G   R   T   T   T   T   P   T   T   T   R

               441                450                459
    GAA CCT AGA CGA CAC CAT CAC CAT CAC CAT TAA 3'
    --- --- --- --- --- --- --- --- --- --- ---
     E   P   R   R   H   H   H   H   H   H   *
```

Fig. 8

```
              9           18          27          36          45          54
5' ATG CCG GTC ATG AGG CTG TTC CCT TGC TTC CTG CAG CTC CTG GCC GGG CTG GCG
   --- --- --- --- --- --- --- --- --- --- --- --- --- --- --- --- --- ---
    M   P   V   M   R   L   F   P   C   F   L   Q   L   L   A   G   L   A

             63          72          81          90          99         108
   CTG CCT GCT GTG CCC CCC CAG CAG TGG GCC TTG TCT GCT GGG AAC GGC TCG TCA
   --- --- --- --- --- --- --- --- --- --- --- --- --- --- --- --- --- ---
    L   P   A   V   P   P   Q   Q   W   A   L   S   A   G   N   G   S   S

            117         126         135         144         153         162
   GAG GTG GAA GTG AAT GAC TGG ATG CGT ACA CTA GAC AAA AGT GGT TGT AAA CCT
   --- --- --- --- --- --- --- --- --- --- --- --- --- --- --- --- --- ---
    E   V   E   V | N   D   W   M   R   T   L   D   K   S   G   C   K   P
         PlGF <---|---> VEGF-E NZ-7
            171         180         189         198         207         216
   AGA GAT ACT GTT GTT TAT TTG GGA GAA GAA TAT CCA GAA AGC ACT AAC CTG CAG
   --- --- --- --- --- --- --- --- --- --- --- --- --- --- --- --- --- ---
    R   D   T   V   V   Y   L   G   E   E   Y   P   E   S   T   N   L   Q

            225         234         243         252         261         270
   TAT AAT CCC CGG TGC GTA ACT GTT AAA CGA TGC AGT GGT TGC TGT AAC GGT GAC
   --- --- --- --- --- --- --- --- --- --- --- --- --- --- --- --- --- ---
    Y   N   P   R   C   V   T   V   K   R   C   S   G   C   C   N   G   D

            279         288         297         306         315         324
   GGT CAA ATA TGT ACA GCG GTT GAA ACA AGA AAT ACA ACT GTA ACA GTT TCA GTA
   --- --- --- --- --- --- --- --- --- --- --- --- --- --- --- --- --- ---
    G   Q   I   C   T   A   V   E   T   R   N   T   T   V   T   V   S   V

            333         342         351         360         369         378
   ACC GGC GTG TCT AGT TCG TCT GGT ACC AAT AGT GGT GTA TCT ACT AAC CTT CAA
   --- --- --- --- --- --- --- --- --- --- --- --- --- --- --- --- --- ---
    T   G   V   S   S   S   S   G   T   N   S   G   V   S   T   N   L   Q

            387         396         405         414         423         432
   AGA ATA AGT GTT ACA GAA CAC ACA AAG TGC GAT TGT ATT GGT AGA ACA ACG ACA
   --- --- --- --- --- --- --- --- --- --- --- --- --- --- --- --- --- ---
    R   I   S   V   T   E   H   T   K   C   D   C   I   G   R   T   T   T

            441         450         459         468         477
   ACA CCT ACG ACC ACT AGG GAA CCT AGA CGA CAC CAT CAC CAT CAC CAT TAA 3'
   --- --- --- --- --- --- --- --- --- --- --- --- --- --- --- --- ---
    T   P   T   T   T   R   E   P   R   R   H   H   H   H   H   H   *
```

Fig.9

```
                9                 18                27                36                45                54
5' ATG AAG TTA ACA GCT ACG TTA CAA GTT GTT GTT GCA TTG TTA ATA TGT ATG TAT
   --- --- --- --- --- --- --- --- --- --- --- --- --- --- --- --- --- ---
    M   K   L   T   A   T   L   Q   V   V   V   A   L   L   I   C   M   Y

                63                72                81                90                99               108
   AAT TTG CCA GAA TGC GTG TCT CAG AGT AAT GAT TCA CCT CCT TCA ACC AAT GAC
   --- --- --- --- --- --- --- --- --- --- --- --- --- --- --- --- --- ---
    N   L   P   E   C   V   S   Q   S   N   D   S   P   P   S   T   N   D

               117               126               135               144               153               162
   TGG ATG CGT ACA CTA GAC AAA AGT GGT TGT AAA CCT AGA GAT ACT GTT GTT TAT
   --- --- --- --- --- --- --- --- --- --- --- --- --- --- --- --- --- ---
    W   M   R   T   L   D   K   S   G   C   K   P   R   D   T   V   V   Y

               171               180               189               198               207               216
   TTG GGA GAA GAA TAT CCA GAA AGC ACT AAC CTG CAG TAT AAT CCC CGG TGC GTA
   --- --- --- --- --- --- --- --- --- --- --- --- --- --- --- --- --- ---
    L   G   E   E   Y   P   E   S   T   N   L   Q   Y   N   P   R   C   V

               225               234               243               252               261               270
   ACT GTT AAA CGA TGC AGT GGT TGC TGT AAC GGT GAC GGT CAA ATA TGT ACA GCG
   --- --- --- --- --- --- --- --- --- --- --- --- --- --- --- --- --- ---
    T   V   K   R   C   S   G   C   C   N   G   D   G   Q   I   C   T   A

               279               288               297               306               315               324
   GTT GAA ACA AGA AAT ACA ACT GTA ACA GTT TCA GTA ACC GGC GTG TCT AGT TCG
   --- --- --- --- --- --- --- --- --- --- --- --- --- --- --- --- --- ---
    V   E   T   R   N   T   T   V   T   V   S   V   T   G   V   S   S   S

               333               342               351               360               369               378
   TCT GGT ACC AAT AGT GGT GTA TCT ACT AAC CTT CAA AGA ATA AGT GTT ACA GAA
   --- --- --- --- --- --- --- --- --- --- --- --- --- --- --- --- --- ---
    S   G   T   N   S   G   V   S   T   N   L   Q   R   I   S   V   T   E

               387               396               405               414               423               432
   CAC ACA AAG TGC GAA TGC CGG CCT CTG CGG GAG AAG ATG AAG CCG GAA AGG TGC
   --- --- --- --- --- --- --- --- --- --- --- --- --- --- --- --- --- ---
    H   T   K   C   E   C   R   P   L   R   E   K   M   K   P   E   R   C
     VEGF-E <----|----> PlGF
               441               450               459               468
   GGC GAT GCT GTT CCC CGG AGG CAC CAT CAC CAT CAC CAT TAA 3'
   --- --- --- --- --- --- --- --- --- --- --- --- --- ---
    G   D   A   V   P   R   R   H   H   H   H   H   H   *
```

Fig.10

```
                 9                18                27                36                45                54
5'  ATG CCG GTC ATG AGG CTG TTC CCT TGC TTC CTG CAG CTC CTG GCC GGG CTG GCG
    --- --- --- --- --- --- --- --- --- --- --- --- --- --- --- --- --- ---
     M   P   V   M   R   L   F   P   C   F   L   Q   L   L   A   G   L   A

                63                72                81                90                99               108
    CTG CCT GCT GTG CCC CCC CAG CAG TGG GCC TTG TCT GCT GGG AAC GGC TCG TCA
    --- --- --- --- --- --- --- --- --- --- --- --- --- --- --- --- --- ---
     L   P   A   V   P   P   Q   Q   W   A   L   S   A   G   N   G   S   S

               117               126               135               144               153               162
    GAG GTG GAA GTG AAT GAC TGG ATG CGT ACA CTA GAC AAA AGT GGT TGT AAA CCT
    --- --- --- --- --- --- --- --- --- --- --- --- --- --- --- --- --- ---
     E   V   E   V | N   D   W   M   R   T   L   D   K   S   G   C   K   P
            PlGF <---|---> VEGF-E
               171               180               189               198               207               216
    AGA GAT ACT GTT GTT TAT TTG GGA GAA GAA TAT CCA GAA AGC ACT AAC CTG CAG
    --- --- --- --- --- --- --- --- --- --- --- --- --- --- --- --- --- ---
     R   D   T   V   V   Y   L   G   E   E   Y   P   E   S   T   N   L   Q

               225               234               243               252               261               270
    TAT AAT CCC CGG TGC GTA ACT GTT AAA CGA TGC AGT GGT TGC TGT AAC GGT GAC
    --- --- --- --- --- --- --- --- --- --- --- --- --- --- --- --- --- ---
     Y   N   P   R   C   V   T   V   K   R   C   S   G   C   C   N   G   D

               279               288               297               306               315               324
    GGT CAA ATA TGT ACA GCG GTT GAA ACA AGA AAT ACA ACT GTA ACA GTT TCA GTA
    --- --- --- --- --- --- --- --- --- --- --- --- --- --- --- --- --- ---
     G   Q   I   C   T   A   V   E   T   R   N   T   T   V   T   V   S   V

               333               342               351               360               369               378
    ACC GGC GTG TCT AGT TCG TCT GGT ACC AAT AGT GGT GTA TCT ACT AAC CTT CAA
    --- --- --- --- --- --- --- --- --- --- --- --- --- --- --- --- --- ---
     T   G   V   S   S   S   S   G   T   N   S   G   V   S   T   N   L   Q

               387               396               405               414               423               432
    AGA ATA AGT GTT ACA GAA CAC ACA AAG TGC GAA TGC CGG CCT CTG CGG GAG AAG
    --- --- --- --- --- --- --- --- --- --- --- --- --- --- --- --- --- ---
     R   I   S   V   T   E   H   T   K   C | E   C   R   P   L   R   E   K
                             VEGF-E <---|---> PlGF
               441               450               459               468               477               486
    ATG AAG CCG GAA AGG TGC GGC GAT GCT GTT CCC CGG AGG CAC CAT CAC CAT CAC
    --- --- --- --- --- --- --- --- --- --- --- --- --- --- --- --- --- ---
     M   K   P   E   R   C   G   D   A   V   P   R   R   H   H   H   H   H

    CAT TAA 3'
    --- ---
     H   *
```

Fig.11

```
          9          18          27          36          45          54
ATG CCG GTC ATG AGG CTG TTC CCT TGC TTC CTG CAG CTC CTG GCC GGG CTG GCG
--- --- --- --- --- --- --- --- --- --- --- --- --- --- --- --- --- ---
 M   P   V   M   R   L   F   P   C   F   L   Q   L   L   A   G   L   A

         63          72          81          90          99         108
CTG CCT GCT GTG CCC CCC CAG CAG TGG GCC TTG TCT GCT GGG AAC GGC TCG TCA
--- --- --- --- --- --- --- --- --- --- --- --- --- --- --- --- --- ---
 L   P   A   V   P   P   Q   Q   W   A   L   S   A   G   N   G   S   S

        117         126         135         144         153         162
GAG GTG GAA GTG GTA CCC TTC CAG GAA GTG TGG GGC CGC AGC TAC TGC CGG GCG
--- --- --- --- --- --- --- --- --- --- --- --- --- --- --- --- --- ---
 E   V   E   V   V   P   F   Q   E   V   W   G   R   S   Y   C   R   A

        171         180         189         198         207         216
CTG GAG AGG CTG GTG GAC GTC GTG TCC GAG TAC CCC AGC GAG GTG GAG CAC ATG
--- --- --- --- --- --- --- --- --- --- --- --- --- --- --- --- --- ---
 L   E   R   L   V   D   V   V   S   E   Y   P   S   E   V   E   H   M

        225         234         243         252         261         270
TTC AGC CCA TCC TGT GTC TCC CTG CTG CGC TGC ACC GGC TGC TGC GGC GAT GAG
--- --- --- --- --- --- --- --- --- --- --- --- --- --- --- --- --- ---
 F   S   P   S   C   V   S   L   L   R   C   T   G   C   C   G   D   E

        279         288         297         306         315         324
AAT CTG CAC TGT GTG CCG GTG GAG ACG GCC AAT GTC ACC ATG CAG CTC CTA AAG
--- --- --- --- --- --- --- --- --- --- --- --- --- --- --- --- --- ---
 N   L   H   C   V   P   V   E   T   A   N   V   T   M   Q   L   L   K

        333         342         351         360         369         378
ATC CGT TCT GGG GAC CGG CCC TCC TAC GTG GAG CTG ACG TTC TCT CAG CAC GTT
--- --- --- --- --- --- --- --- --- --- --- --- --- --- --- --- --- ---
 I   R   S   G   D   R   P   S   Y   V   E   L   T   F   S   Q   H   V

        387         396         405         414         423         432
CGC TGC GAA TGC CGG CCT CTG CGG GAG AAG ATG AAG CCG GAA AGG TGC GGC GAT
--- --- --- --- --- --- --- --- --- --- --- --- --- --- --- --- --- ---
 R   C   E   C   R   P   L   R   E   K   M   K   P   E   R   C   G   D

        441         450         459         468
GCT GTT CCC CGG AGG CAC CAT CAC CAT CAC CAT TAA 3'
--- --- --- --- --- --- --- --- --- --- --- ---
 A   V   P   R   R   H   H   H   H   H   H   *
```

CHIMERIC HUMAN-TYPE VASCULAR ENDOTHELIAL CELL GROWTH FACTOR

TECHNICAL FIELD

The present invention relates to chimera vascular endothelial growth factors (VEGF). More particularly, the present invention relates to a chimera protein having an activity of growing vascular endothelial cells, which is obtained by substituting a part of the sequence of a VEGF analogous protein having an activity of vascularization that binds to KDR (VEGF receptor-2) but does not bind to Flt-1 (VEGF receptor-1) with a corresponding sequence of a human-derived VEGF analogous protein. The present invention also relates to a medicament comprising the chimera protein, DNA encoding the chimera protein, an expression vector comprising the DNA, a medicament comprising the expression vector, a transformant having the expression vector, and a process for producing the chimera protein using the transformant

BACKGROUND ART

Circulatory disorders caused by vascular system abnormalities are observed in numerous diseases, and specific examples of such diseases include angina pectoris, heart infarction, lower extremity circulatory failure caused by diabetes, and arterial occlusive disease. These diseases not only impart a great deal of pain to patients but also often lead patients to death. In order to overcome this problem, a great deal of research has been conducted regarding vascularization, and as a result, vascular endothelial growth factors (hereinafter abbreviated to "VEGF") and their receptors (Flt-1, KDR) were found to play central roles therein (Ferara N. and Davis-Smyth T., Endocrine Review, 18, 4-25, 1997, Shibuya M., Advances in Cancer Research, 67, 281-316, 1995).

A possible method to ameliorate various circulatory failures is carried out by administering VEGF, an analogous protein thereof, or a vector for expressing them into subcutaneous tissue or muscular tissue of cardiac muscle or lower extremity to accelerate vascularization by these vascularization factors. Clinical experiments on VEGF have already started, and VEGF are known to bind to and activate both Flt-1 (VEGF receptor-1) and KDR (VEGF receptor-2) (Shibuya M. et al. Current Topics in Microbiology and Immunology, 237, 59-83, 1999). Approximately 90% of vascularization signals are sent from KDR (VEGF receptor-2) (Takahashi T. et al. Oncogene, 18, 2221-2230, 1999), while Flt-1 (VEGF receptor-1) sends out signals for the chemotaxis of monocytes and macrophages and relatively weak vascularization signals (Barleon B. et al. Blood, 87, 3336-3343, 1996, Clauss M. et al. Journal of Biological Chemistry, 271, 17629-17634, 1996). Monocytes and macrophage cells are known to secrete various cytokines and the like to induce inflammation, and are likely to disturb vascularization therapy. Accordingly, a VEGF analogous protein which binds to only KDR (VEGF receptor-2) and can activate it, is understood as more suitable for vascularization therapy. VEGF-$E_{NZ\text{-}7}$ was reported as a protein that binds to only KDR (VEGF receptor-2) (Ogawa S. et al. Journal of Biological Chemistry, 273, 31273-31282, 1998). Although this gene per se was found in the Orf virus genome of Parapox in 1994, its property still remains unknown, and its characteristic features that it binds to only KDR (VEGF receptor-2) and has potent vascularization activity were elucidated for the first time by Ogawa et al. (Lyttle D. J. et al. Journal of Virology, 68, 84-92, 1994; Ogawa S. et al. Journal of Biological Chemistry, 273, 31273-31282, 1998).

Thereafter, VEGF-$E_{D1701}$ and VEGF-$E_{NZ\text{-}2}$, which are allied with VEGF-$E_{NZ\text{-}7}$, were similarly reported as binding to only KDR (VEGF receptor-2) (FIG. 1) (Meyer M. et al. EMBO Journal 18, 363-374, 1999). As described above, VEGF-$E_{NZ\text{-}7}$ binds to only KDR (VEGF receptor-2), has substantially the same vascularization activity as VEGF, and does not stimulate the chemotaxis of monocytes and macrophages.

DISCLOSURE OF THE INVENTION

As mentioned above, VEGF-$E_{NZ\text{-}7}$ is considered to be a protein which is clinically highly applicable, but it has some drawbacks remaining to be solved, i.e., reduction or elimination of antigenicity. Specifically, since the VEGF-$E_{NZ\text{-}7}$ gene is not derived from human genome, its product, the VEGF-$E_{NZ\text{-}7}$ protein, is regarded as a foreign substance which has a certain degree of antigenicity to the human immune system, and thus there is a possibility that antibodies would be generated. Accordingly, although a potent vascularization effect can be expected at the early stage of administration, if the antibody is generated in the individual patient it is predicted that VEGF-$E_{NZ\text{-}7}$ may be absorbed by the antibody even though it is readministered and its effect would deteriorate.

Specifically, an object of the present invention is to provide a chimera VEGF-E having a reduced antigenicity while maintaining the activity of VEGF-E. Further, it is another object of the present invention to provide a medicament comprising the chimera VEGF-E, DNA encoding the chimera VEGF-E, and a process for producing the chimera VEGF-E using the DNA.

The present inventor has conducted concentrated studies in order to attain the above objects. As a result, they succeeded in reducing and eliminating only antigenicity and foreign property while maintaining VEGF-$E_{NZ\text{-}7}$ activity by separating, by means of domain analysis, a portion which is involved in the VEGF-$E_{NZ\text{-}7}$ activity from a portion which is expected to have relatively high antigenicity, and substituting the portion expected to have relatively high antigenicity with a known human protein. This has led to the completion of the present invention.

Thus, the present invention provides a chimera protein having an activity of growing vascular endothelial cells, which is obtained by substituting a part of the sequence of a VEGF analogous protein having an activity of vascularization that binds to KDR (VEGF receptor-2) but does not bind to Flt-1 (VEGF receptor-1) with a corresponding sequence of a human-derived VEGF analogous protein.

One aspect of the present invention provides a chimera protein having an activity of growing vascular endothelial cells, which is obtained by substituting the amino terminus and/or carboxyl terminus of a VEGF analogous protein having an activity of vascularization that binds to KDR (VEGF receptor-2) but does not bind to Flt-1 (VEGF receptor-1) with the amino terminus and/or carboxyl terminus of a human-derived VEGF analogous protein, respectively. Preferably, there is provided a chimera protein obtained by substituting 10 to 50 amino acid residues at the amino terminus of a VEGF analogous protein having an activity of vascularization that binds to KDR (VEGF receptor-2) but does not bind to Flt-1 (VEGF receptor-1) with the amino terminus of a human-derived VEGF analogous protein and/or substituting 10 to 50 amino acid residues at the carboxyl terminus of the VEGF analogous protein with the carboxyl terminus of the human-derived VEGF analogous protein.

Another aspect of the present invention provides a chimera protein having an activity of growing vascular endothelial cells, which is obtained by substituting a part of the internal sequence of a VEGF analogous protein having an activity of vascularization that binds to KDR (VEGF receptor-2) but does not bind to Flt-1 (VEGF receptor-1) with a corresponding sequence of a human-derived VEGF analogous protein. Preferably, there is provided a chimera protein which is obtained by substituting a part of the sequence of a VEGF analogous protein having an activity of vascularization that binds to KDR (VEGF receptor-2) but does not bind to Flt-1 (VEGF receptor-1) with a human-derived VEGF analogous protein in such a way that at least the sequences of the loop 1 region (amino acid residues 47 to 80) and the loop 3 region (amino acid residues 89 to 132) of the VEGF analogous protein are maintained.

Preferably, a VEGF analogous protein having an activity of vascularization that binds to KDR (VEGF receptor-2) but does not bind to Flt-1 (VEGF receptor-1) belongs to the VEGF-E family. More preferably, it is VEGF-$E_{NZ-7}$, VEGF-$E_{D1701}$, or VEGF-$E_{NZ-2}$.

Preferably, a human-derived VEGF analogous protein is PIGF.

Preferably, the chimera protein of the present invention is obtained by substituting 10 to 50 amino acid residues at the carboxyl terminus of a VEGF analogous protein having an activity of vascularization that binds to KDR (VEGF receptor-2) but does not bind to Flt-1 (VEGF receptor-1) with the carboxyl terminus of a human-derived VEGF analogous protein.

Preferably in the chimera protein of the present invention, the VEGF analogous protein having an activity of vascularization that binds to KDR (VEGF receptor-2) but does not bind to Flt-1 (VEGF receptor-1) belongs to the VEGF-E family, and the loop 1 region of amino acid residues 47 to 80 and the loop 3 region of amino acid residues 89 to 132 in the protein belonging to the VEGF-E family are substantially retained.

According to embodiments of the present invention, there is provided a chimera protein having any of the following amino acid sequences:

(A) the amino acid sequence as shown in SEQ ID NO: 8, 9, or 10;

(B) an amino acid sequence derived from the amino acid sequence as shown in SEQ ID NO: 8, 9, or 10 by deletion, substitution, and/or addition of one or several amino acids and having an activity of growing vascular endothelial cells; and (C) an amino acid sequence having 60% or more homology to the amino acid sequence as shown in SEQ ID NO: 8, 9, or 10 and having an activity of growing vascular endothelial cells.

Embodiments of the present invention provide a chimera protein comprising: any of the amino acid sequences as shown in (A) to (F) below; an amino acid sequence derived from any of the amino acid sequences as shown in (A) to (F) below by deletion, substitution, and/or addition of one or several amino acids and having an activity of growing vascular endothelial cells; or an amino acid sequence having 60% or more homology to any of the amino acid sequences as shown in (A) to (F) below and having an activity of growing vascular endothelial cells.

(A) an amino acid sequence obtained by substituting the sequence Tyr-Leu-Gly-Glu (amino acids 54 to 57 of SEQ ID NO: 7) with Asp-Val-Val-Ser (SEQ ID NO: 21) in the amino acid sequence as shown in SEQ ID NO: 7;

(B) an amino acid sequence obtained by substituting the sequence Ser-Thr-Asn (amino acids 62 to 64) with Glu-Val-Glu in the amino acid sequence as shown in SEQ ID NO: 7;

(C) an amino acid sequence obtained by substituting the sequence Leu-Gln-Tyr-Asn (amino acids 65 to 68 of SEQ ID NO: 7) with His-Met-Phe-Ser (SEQ ID NO: 22) in the amino acid sequence as shown in SEQ ID NO: 7;

(D) an amino acid sequence obtained by substituting the sequence Trp-Met-Arg-Thr-Leu-Asp-Lys (amino acids 37 to 43 of SEQ ID NO: 7) with Phe-Gln-Glu-Val-Trp-Gly-Arg (SEQ ID NO: 23) in the amino acid sequence as shown in SEQ ID NO: 7;

(E) an amino acid sequence obtained by substituting the sequence Lys-Pro-Arg-Asp-Thr-Val (amino acids 47 to 52 of SEQ ID NO: 7) with Arg-Ala-Leu-Glu-Arg-Leu (SEQ ID NO: 24) in the amino acid sequence as shown in SEQ ID NO: 7; or (F) an amino acid sequence obtained by substituting the sequence Leu-Gln-Arg-Ile (amino acids 119 to 122of SEQ ID NO: 7) with Tyr-Val-Glu-Leu (SEQ ID NO: 25) in the amino acid sequence as shown in SEQ ID NO: 7.

Embodiments of the present invention provide a chimera protein which has any of the amino acid sequences shown below:

(A) an amino acid sequence as shown in SEQ ID NO: 15;

(B) an amino acid sequence derived from the amino acid sequence as shown in SEQ ID NO: 15 by deletion, substitution, and/or addition of one or several amino acids and having an activity of growing vascular endothelial cells; and (C) an amino acid sequence having 60% or more homology to the amino acid sequence as shown in SEQ ID NO: 15 and having an activity of growing vascular endothelial cells.

Another aspect of the present invention provides a medicament comprising any of the aforementioned chimera proteins of the present invention.

A further aspect of the present invention provides an activator for KDR (VEGF receptor-2) receptor comprising any of the chimera proteins of the present invention.

A further aspect of the present invention provides an agent for growing vascular endothelial cells comprising any of the chimera proteins of the present invention.

A further aspect of the present invention provides DNA encoding any of the chimera proteins of the present invention.

A further aspect of the present invention provides an expression vector comprising the DNA according to the present invention.

A further aspect of the present invention provides a medicament comprising the expression vector according to the present invention.

A further aspect of the present invention provides an activator for KDR (VEGF receptor-2) receptor comprising the expression vector according to the present invention.

A further aspect of the present invention provides an agent for growing vascular endothelial cells comprising the expression vector according to the present invention.

A further aspect of the present invention provides a transformant having the expression vector according to the present invention.

A further aspect of the present invention provides a process for producing any of the chimera proteins of the present invention wherein the transformant according to the present invention is used.

BRIEF DESCRIPTION OF DRAWINGS

FIG. 7 shows the nucleotide sequence (SEQ ID NO: 16) and the amino acid sequence (SEQ ID NO: 7) of VEGF-E-His.

FIG. 8 shows the nucleotide sequence (SEQ ID NO: 17) and the amino acid sequence (SEQ ID NO: 8) of VEGF-E-NP-His.

FIG. 9 shows the nucleotide sequence (SEQ ID NO: 18) and the amino acid sequence (SEQ ID NO: 9) of VEGF-E-CP-His.

FIG. 10 shows the nucleotide sequence (SEQ ID NO: 19) and the amino acid sequence of (SEQ ID NO: 10) VEGF-E-NP/CP-His.

FIG. 11 shows the nucleotide sequence (SEQ ID NO: 20) and the amino acid sequence of (SEQ ID NO: 11) hPIGF-I-His.

BEST MODES FOR CARRYING OUT THE INVENTION

Figure 1:
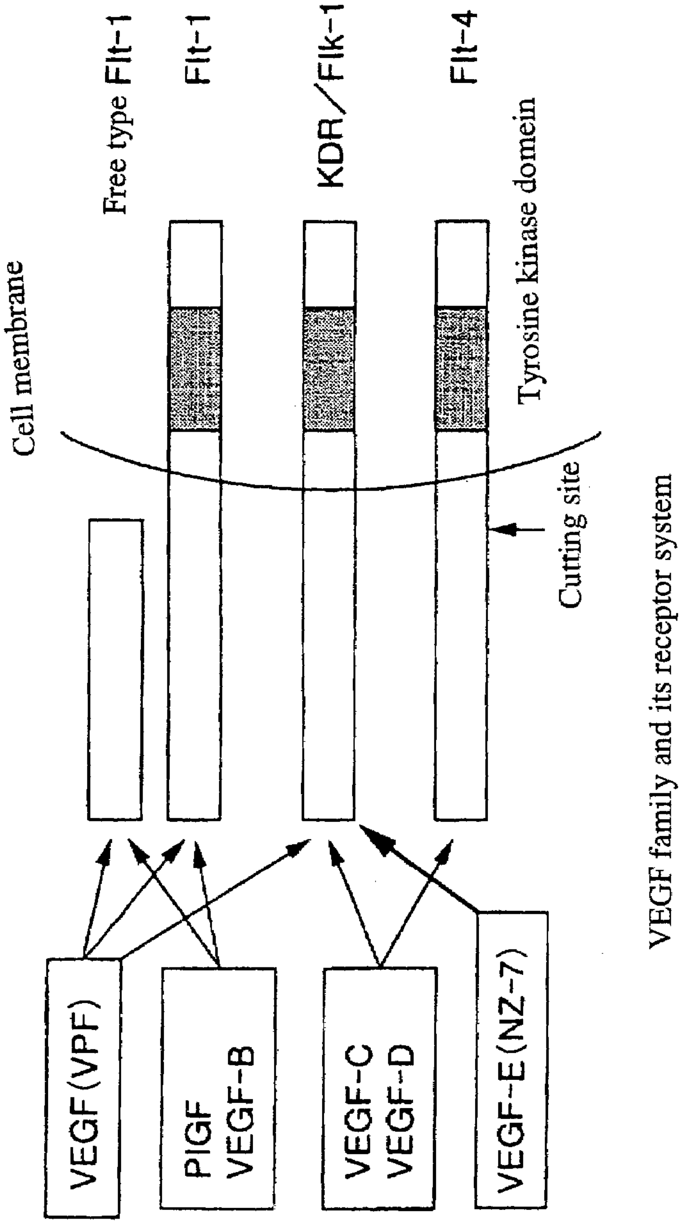
FIG. 1 shows an interrelationship between VEGF-$E_{N27}$ protein and VEGF receptor.

Processes and embodiments for carrying out the present invention are hereafter described in detail.

(1) Chimera Protein Having an Activity of Growing Vascular Endothelial Cells

The chimera protein having an activity of growing vascular endothelial cells according to the present invention can be obtained by substituting a part of the sequence of a VEGF analogous protein having an activity of vascularization that binds to KDR (VEGF receptor-2) but does not bind to Flt-1 (VEGF receptor-1) with a corresponding sequence of a human-derived VEGF analogous protein.

The type of VEGF analogous protein having an activity of vascularization that binds to KDR (VEGF receptor-2) but does not bind to Flt-1 (VEGF receptor-1) is not particularly limited, and specific examples thereof include a protein belonging to the VEGF-E family. More specific examples include VEGF-$E_{NZ-7}$, VEGF-$E_{D1701}$, and VEGF-$E_{NZ-2}$ (Ogawa S. et al. Journal of Biological Chemistry, 273, 31273-31282, 1998; and Meyer M. et al. EMBO Journal 18, 363-374, 1999).

In one embodiment of the chimera protein of the present invention, the amino terminus and/or carboxyl terminus of a VEGF analogous protein having an activity of vascularization is substituted with the amino terminus and/or carboxyl terminus of a human-derived VEGF analogous protein. The region that is substituted with the human-derived VEGF analogous protein may be only the amino terminus or only the carboxyl terminus of the VEGF analogous protein, or may be both the amino and carboxyl termini. The length of the amino terminus to be substituted is not particularly limited as long as the resulting chimera protein remains the activity of growing vascular endothelial cells. Preferably 10 to 50 amino acid residues, more preferably 20 to 40 amino acid residues, and particularly preferably 20 to 30 amino acid residues at the amino terminus are substituted with the amino terminus of a human-derived VEGF analogous protein. Similarly, the length of the carboxyl terminus to be substituted is not particularly limited as long as the resulting chimera protein remains the activity of growing vascular endothelial cells. Preferably 10 to 50 amino acid residues, more preferably 10 to 40 amino acid residues, further preferably 10 to 30 amino acid residues, and particularly preferably 10 to 20 amino acid residues at the carboxyl terminus are substituted with the carboxyl terminus of a human-derived VEGF analogous protein.

In another embodiment of the chimera protein of the present invention, a part of the internal sequence of a VEGF analogous protein having an activity of vascularization that binds to KDR (VEGF receptor-2) but does not bind to Flt-1 (VEGF receptor-1) is substituted with a corresponding sequence of a human-derived VEGF analogous protein. Preferably, a part of the sequence of a VEGF analogous protein having an activity of vascularization that binds to KDR (VEGF receptor-2) but does not bind to Flt-1 (VEGF receptor-1) is substituted with a human-derived VEGF analogous protein in such a way that at least the sequences of the loop 1 region (amino acid residues 47 to 80) and the loop 3 region (amino acid residues 89 to 132) of the VEGF analogous protein are maintained.

In another embodiment of the chimera protein of the present invention, the amino terminus and/or carboxyl terminus of a VEGF analogous protein having an activity of vascularization is substituted with the amino terminus and/or carboxyl terminus of a human-derived VEGF analogous protein, and at the same time, a part of the internal sequence of the VEGF analogous protein is substituted with a corresponding sequence of the human-derived VEGF analogous protein.

Preferably, the VEGF analogous protein having an activity of vascularization according to the present invention belongs to the VEGF-E family. VEGF-E is a protein of 149 amino acids, and is composed of:

(I) the amino terminal region comprising a signal peptide (amino acid residues 1 to 46);

(II) loop 1 region (amino acid residues 47 to 80);

(III) loop 2 region (amino acid residues 81 to 88);

(IV) loop 3 region (amino acid residues 89 to 132); and (V) the carboxyl terminal region (amino acid residues 133 to 148) (Ogawa S. et al., Journal of Biological Chemistry, 273, 31273-31282, 1998). Among the aforementioned regions, since the importance of the loop 3 region in binding with KDR (VEGF receptor-2) is suggested, it is preferred that the chimera protein of the present invention substantially maintains the loop 3 region of amino acid residues 89 to 132 of VEGF-E.

The chimera protein of the present invention is obtained by substituting the amino terminus and/or carboxyl terminus of a VEGF analogous protein with the amino terminus and/or carboxyl terminus of a human-derived VEGF analogous protein, respectively. This can lower the antigenicity of the VEGF analogous protein. The types of human-derived VEGF analogous proteins are not particularly limited, and examples thereof include PIGF, and particularly, hPIGF1.

The aforementioned chimera proteins may have addition, deletion, substitution, and/or modification in a portion of their amino acid sequence, as long as the proteins remain the activity of growing vascular endothelial cells.

Specific examples of the chimera proteins of the present invention include those having any of the following amino acid sequences:

(A) the amino acid sequence as shown in SEQ ID NO: 8, 9, 10, or 15 or the amino acid sequence having the substitution specified herein in the amino acid sequence of SEQ ID NO: 7;

(B) an amino acid sequence derived from the amino acid sequences as defined in (A) by deletion, substitution, and/or addition of one or several amino acids and having an activity of growing vascular endothelial cells; and (C) an amino acid sequence having 60% or more homology to the amino acid sequences as defined in (A) and having an activity of growing vascular endothelial cells.

The phrase "an amino acid sequence derived from . . . by deletion, substitution, and/or addition of one or several amino acids" used herein refers to an amino acid sequence in which, for example, 1 to 20, preferably 1 to 15, more preferably 1 to 10, and further preferably 1 to 5 amino acids are deleted, substituted, and/or added.

The term "the amino acid sequence having 60% or more homology to the amino acid sequence" used herein refers to having homology of at least 60%. Homology is preferably 70% or more, more preferably 80% or more, further preferably 90% or more, and particularly preferably 95% or more.

The proteins which have an amino acid sequence derived from a certain amino acid sequence by deletion, substitution, and/or addition of one or several amino acids and having an activity of growing vascular endothelial cells or an amino acid sequence having 60% or more homology with a certain amino acid sequence and having an activity of growing vascular endothelial cells, can be produced or obtained using common recombinant techniques (including site-specific mutagenesis) described in, for example, Molecular Cloning, A Laboratory Manual, Second Edition, Cold Spring Harbor Laboratory Press (1989), or Current Protocols in Molecular Biology, John Wiley & Sons (1987-1997) and using DNA encoding a protein having an amino acid sequence as shown in any of SEQ ID Nos: 7 to 11.

(2) Process for Producing Chimera Protein Having an Activity of Growing Vascular Endothelial Cells A process for producing the chimera protein of the present invention is hereafter described in detail.

A gene encoding a VEGF analogous protein (e.g., the VEGF-E gene) that binds to KDR (VEGF receptor-2) but does not bind to Flt-1 (VEGF receptor-1) and has an activity of vascularization or a modified gene thereof is used as a starting material, and DNA fragment is cut out using a suitable restriction enzyme. Alternatively, a desired DNA fragment which encodes the VEGF analogous protein is prepared by PCR or the like.

Separately, DNA which encodes the amino terminus and/or carboxyl terminus of the human-derived VEGF analogous protein to be substituted or a partial internal sequence thereof is prepared. The DNA which encodes the amino terminus and/or carboxyl terminus of the human-derived VEGF analogous protein or a partial internal sequence thereof may be obtained by cleaving out a desired DNA fragment using a suitable restriction enzyme from a gene encoding the human-derived VEGF analogous protein. Alternatively, a desired DNA fragment may by amplified by PCR or may be obtained by chemical synthesis using a DNA synthesizer.

Subsequently, the DNA fragments obtained above can be bound to each other using a suitable DNA ligase. In this case, an oligonucleotide may be inserted to align the reading flames, or a part of the nucleotide sequence may be altered to create an identical restriction site.

Any plasmid to which DNA is to be inserted can be used as long as it can be replicated and retained in a host, and examples include pBR322 and pUC18 derived from *Escherichia coli*, and pET-3c constructed based thereon.

Examples of methods for inserting DNA into plasmid include a method described in T. Maniatis et al., Molecular Cloning, Cold Spring Harbor Laboratory, p. 239 (1982).

A cloned gene encoding a chimera protein can be used to construct an expression vector by ligating the gene downstream of the promoter in a vector which is suitable for expression.

Examples of expression vectors that can be used in the present invention include: the plasmid derived from *Escherichia coli* (pBR322, pBR325, pUC12, pUC13, pET-3); plasmid derived from *Bacillus subtilis* (pUB110, pTP5, pC194); plasmid derived from yeast (pSH19, pSH15); bacteriophage such as λphage or its derivative; animal viruses such as retrovirus and vaccinia virus; and insect viruses (e.g., baculovirus).

The gene may have at its 5' terminus ATG as a translation initiation codon, and may have at its 3' terminus TAA, TGA, or TAG as a translation termination codon. In order to express the gene, a promoter is connected upstream thereof. Any promoter can be used in the present invention as long as it is suitable in respect of the host that is used in the gene expression.

When the host for transformation is *Escherichia coli*, trp promoter, lac promoter, rec A promoter, λ PL promoter, 1pp promoter, T7 promoter, and the like are preferable. When a host is *Bacillus subtilis*, SP01 promoter, SP02 promoter, penP promoter, and the like are preferable. When a host is yeast, PHO5 promoter, PGK promoter, GAP promoter, ADH promoter, and the like are preferable. When a host is an animal cell, preferable promoters include SV40-derived promoter and a retrovirus promoter.

A vector comprising recombinant DNA having DNA encoding the chimera protein of the present invention thus prepared is used to prepare a transformant which has the vector.

Examples of hosts include *Escherichia coli* (e.g., BL21, BL21(DE3), BL21(DE3)pLysS, and BL21(DE3)pLysE), *Bacillus subtilis* (e.g., *Bacillus subtilis* DB105), yeast (e.g., *Pichia pastoris,* and *Saccharomyces cerevisiae*), animal cells (e.g., COS cell, CHO cell, BHK cell, NIH3T3 cell, BALB/c3T3 cell, HUVE cell, and LEII cell), and insect cells.

The aforementioned transformation can be carried out in accordance with commonly employed methods regarding each host. For example, when a host is *Escherichia coli*, a vector comprising recombinant DNA is introduced by the heat shock method, electroporation, or the like into a competent cell that was prepared by the calcium method or other methods. When a host is yeast, a vector comprising recombinant DNA is introduced by the heat shock method, electroporation, or the like into a competent cell that was prepared by the lithium method or other methods. When a host is an animal cell, a vector comprising recombinant DNA is introduced into a cell by the calcium phosphate method, lipofection method, electroporation method, or the like.

A transformant which has an expression vector comprising DNA that encodes the chimera protein of the present invention can be obtained by the above method. The chimera protein of the present invention can be produced by culturing the transformant in a suitable medium.

When a transformant is cultured, a commonly used medium can be used for each host. For example, LB Medium can be used in the case of *Escherichia coli*, YPD Medium can be used in the case of yeast, and a medium prepared by adding animal serum to Dulbecco's MEM can be used in the case of the animal cell.

A transformant can be cultured under general conditions for each host For example, when a host is *Escherichia coli*, culturing is conducted at about 30 to 37° C. for about 3 to 24 hours, and if necessary, aeration or agitation can be applied. When a host is yeast, culturing is conducted at about 25 to 37° C. for about 12 hours to 2 weeks, and if necessary, aeration or agitation can be applied. When a host is an animal cell, culturing is conducted at about 32 to 37° C. under 5% $CO_2$ and 100% humidity for about 24 hours to 2 weeks, and if necessary, the condition of the gas phase can be altered or agitation can be applied.

When the chimera protein of the present invention is expressed using an insect cell as a host, a protein can be expressed in accordance with the method described in, for example, Baculovirus Expression Vectors, A Laboratory Manual; Current Protocols in Molecular Biology; and Bio/Technology, 6, 47 (1988).

Specifically, a recombinant gene-introduced vector and baculovirus are co-introduced into an insect cell so as to obtain a recombinant virus in a culture supernatant of the insect cell. Thereafter, the insect cell is further infected with the recombinant virus, thereby expressing the protein.

Examples of a vector for introducing the gene that is used in the above method include pVL1392, pVL1393, and pBlueBacIII (all available from Invitrogen).

As the baculovirus, for example, *Autographa californica* nuclear polyhedrosis virus, which is a virus infecting an insect belonging to the genus Mamestra, can be used.

As the insect cell, for example, ovarian cells of *Spodoptera frugiperda*, Sf9 and Sf21 (Baculovirus Expression Vectors, A Laboratory Manual, W. H. Freeman and Company, New York, 1992) and an ovarian cell of *Trichoplusia ni*, High5, (Invitrogen) can be used.

Examples of methods for co-introducing the recombinant gene-introduced vector and the baculovirus in the insect cell for the preparation of the recombinant virus include the calcium phosphate method (JP Patent Publication (Unexamined Application) No. 2-227075) and lipofection method (Proc. Natl. Acad. Sci. USA, 84, 7413(1987)).

Medium that can be used for culturing the transformant obtained by using the insect cell as a host cell includes commonly used TNM-FH medium (Pharmingen), Sf-900 II SFM medium (GIBCO BRL), ExCell 400 and ExCell 405 (JRH Biosciences), and Grace's Insect Medium (Grace, T. C. C., Nature, 195, 788 (1962)). Culturing is generally conducted under conditions of, for example, pH 6 to 7 at 25 to 30° C. for 1 to 5 days. If necessary, an antibiotic such as gentamicin may be added to the medium during the culture.

In order to extract the chimera protein of the present invention from the microorganisms or cell of the aforementioned culture product, the chimera protein may be directly purified from the culture supernatant, or alternatively after culturing of the transformant, microorganisms or cells are disrupted by means of a homogenizer, French press, ultrasound, lysozyme, and/or freeze and thawing to eluate the chimera protein of interest extracellularly, and thereby obtain the chimera protein from the soluble fraction. When a chimera protein of interest is contained in insoluble fractions, a method for collecting bacterial bodies or cells can be performed by first disrupting bacterial bodies or cells, collecting insoluble fractions by centrifugation, and solubilizing them by a buffer comprising guanidine hydrochloride and the like. Alternatively, bacterial bodies or cells are directly disrupted by a buffer comprising a protein denaturing agent such as guanidin hydrochloride to eluate the chimera protein of interest extracellularly.

The chimera protein of the present invention can be purified from the aforementioned soluble fractions by suitably combining conventional separation and purification methods. Examples of such methods include salting-out, solvent precipitation, dialysis, ultrafiltration, gel filtration, SDS-polyacrylamide gel electrophoresis, ion-exchange chromatography, affinity chromatography, reverse phase high-performance liquid chromatography, and isoelectric focusing.

When a histidine tag is fused with the chimera protein of the present invention and the fused protein is expressed, a nickel carrier such as Ni-NTA agarose can be used to specifically adsorb the histidine tag-fused chimera protein for the recovery.

(3) Medicament Comprising a Chimera Protein Having an Activity of Growing Vascular Endothelial Cells or an Expression Vector Comprising DNA Encoding a Chimera Protein Having an Activity of Growing Vascular Endothelial Cells The chimera protein of the present invention has an activity of growing vascular endothelial cells. Circulatory disorders caused by a vascular system abnormality are observed in numerous diseases, and specific examples of such diseases include angina pectoris, heart infarction, lower extremity circulatory failures caused by diabetes, and arterial occlusive diseases. Administration of the chimera protein of the present invention or an expression vector comprising DNA encoding the chimera protein to the patients suffering from the aforementioned diseases can impart therapeutic effects through the growth action on vascular endothelial cells. Since the chimera protein of the present invention can activate the KDR (VEGF receptor-2) receptor, it is also useful as a therapeutic or preventive agent for diseases involving abnormality in the activity of the KDR (VEGF receptor-2) receptor.

As described above, the chimera protein of the present invention is useful as a medicament.

The chimera protein of the present invention can be formulated into pharmaceutical compositions such as solutions, injections, powders, granules, tablets, suppositories, enteric pills or tablets, and capsules by using, for example, a pharmaceutically acceptable solvent, excipient, carrier, and adjuvant in accordance with conventional techniques.

The content of the chimera protein of the present invention which is an active ingredient in the pharmaceutical composition may be about 0.000001 to 1.0% by weight. These pharmaceutical compositions can be safely administered to mammalian animals such as human, mouse, rat, rabbit, dog, and cat, and particularly preferably to human as an activator for KDR (VEGF receptor-2) receptor or an agent for growing vascular endothelial cells. Any route of administration such as local, oral, parenteral intranasal, intravenous, intramuscular, subcutaneous, or percutaneous administration can be employed.

The dose of the chimera protein of the present invention should be properly increased or decreased depending on conditions such as age, sex, weight, or symptom of the patient, and route of administration. For example, when administered to mammalian animals including human, the chimera protein can be administered in an amount of approximately 0.01 μg to 10 mg/kg (body weight) per day.

An expression vector comprising DNA encoding the chimera protein of the present invention can be formulated in order to be administered in any route of administration such as local oral, parenteral intranasal, intravenous, intramuscular, subcutaneous, or percutaneous administration. Preferably, the expression vector is used in a form of injection. For example, the expression vector of the present invention can be mixed with a pharmaceutically acceptable excipient to prepare an injection. Examples of injections include an aseptic solution and an isotonic solution. Alternatively, it can be formulated as a dry composition, particularly as a freeze-dried composition, and these can be formulated into an injection by adding sterilized water or physiological saline at the time of use thereof.

The dose of the expression vector of the present invention should be properly increased or decreased depending on conditions such as age, sex, weight, or symptom of the patient, and route of administration. In general the amount of DNA as an active ingredient is in the range of about 1 μg/kg to 1000 mg/kg per day per adult, and preferably in the range of about 10 μg to 100 mg/kg per day per adult.

The present invention will be described in more detail with reference to the following examples, but the present invention is not limited by these examples.

EXAMPLES

Example 1

Cells and Culture Conditions

Ex-Cell 400 (JRH Biosciences, Lenexa, Kans.) was used as a culture solution for Sf9 insect cells (Invitrogen, Calif., USA). NIH3T3 mouse fibroblast and a cell strain NIH3T3-KDR which strongly expresses a human VEGF receptor, KDR (VEGFR-2), were used in the experiment for assaying the KDR autophosphorylation by ligand binding. The NIH3T3-KDR cell was produced by Sawano et al. (Sawano A. et al. Cell growth and Differentiation, 7, 213-221, 1996). The NIH3T3 cell and the NIH3T3-KDR cell were maintained in a medium obtained by adding 10% bovine serum, 2 mM L-glutamine, and 200 μg/ml G418 (Geneticin; Life Technologies, Inc., Grand Island, N.Y.) to Dulbecco's Modified Eagle's Medium (DMEM, Nissui, Tokyo). Human umbilical vein endothelial cells (HUVEC, Morinaga, Tokyo) were maintained in HUVE culture medium (Morinaga, Tokyo) and used in the assay for the endothelial cell growth. Recombinant human $VEGF_{165}$ was forcibly expressed in the Sf9 cells by baculovirus system and then purified from the culture supernatant using a haparin column and used. Fc-fused 7N-sKDR (free KDR) was used in the experiment for ligand binding (Shinkai A. et al. J. Biol. Chem. 273, 31283-31288, 1998).

Example 2

Production of Mutant Chimera VEGF-$E_{N27}$ proteins (VEGF-E-NP, VEGF-E-CP, VEGF-E-NP/CP)

Figure 2:
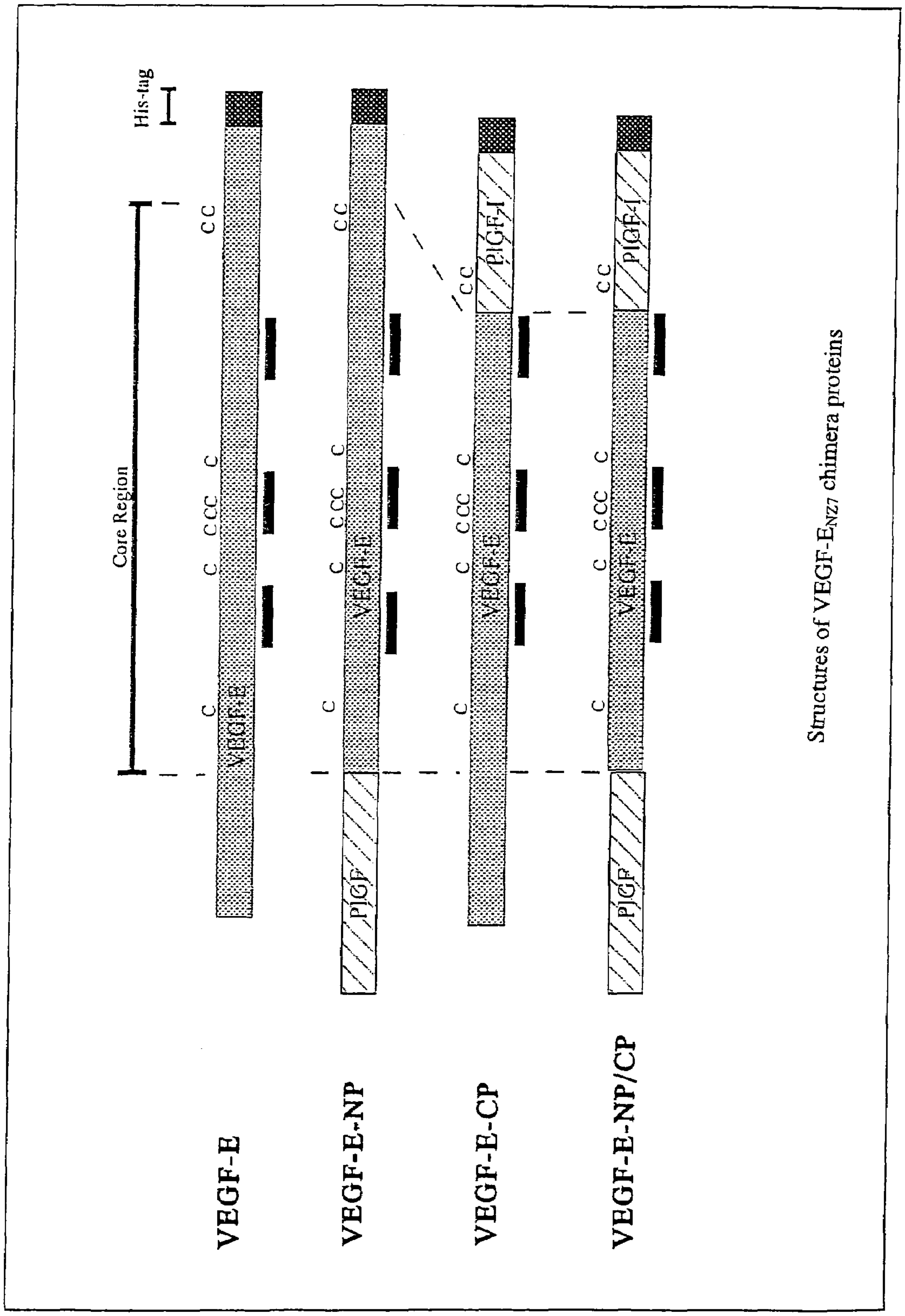
FIG. 2 shows the structures of VEGF-$E_{N27}$ chimera proteins (VEGF-E-NP, VEGF-E-CP, VEGF-E-NP/CP).

The following three types of VEGF-$E_{N27}$/human PIGF-1 (hereinafter referred to as "hPIGF-1") chimera proteins were produced (FIG. 2):

(1) chimera protein VEGF-E-NP prepared by substituting 34 amino acid residues at the amino terminus of VEGF-$E_{N27}$ with 40 amino acid residues at the amino terminus of hPIGF-1;

(2) VEGF-E-CP prepared by substituting 18 amino acid residues at the carboxyl terminus of VEGF-$E_{N27}$ with 21 amino acid residues at the carboxyl terminus of hPIGF-1; and (3) VEGF-E-NP/CP prepared by substituting both the amino and carboxyl terminuses of VEGF-$E_{N27}$ with those of hPIGF-1.

The above three types of chimera proteins were fused with histidine tags to simplify the purification. The method in which DNA encoding each chimera protein was prepared and subcloned into vector pUC18 is described below.

The nucleotide sequence and the amino acid sequence of VEGF-E-His are shown in FIG. 7 and SEQ ID NO: 7, the nucleotide sequence and the amino acid sequence of VEGF-E-NP-His are shown in FIG. 8 and SEQ ID NO: 8, the nucleotide sequence and the amino acid sequence of VEGF-E-CP-His are shown in FIG. 9 and SEQ ID NO: 9, the nucleotide sequence and the amino acid sequence of VEGF-E-NP/CP-His are shown in FIG. 10 and SEQ ID NO: 10, and the nucleotide sequence and the amino acid sequence of hPIGF-I-His are shown in FIG. 11 and SEQ ID NO: 11. (VEGF-E-CP and VEGF-E-NP)

pUC18-VEGF-E-His, which is plasmid DNA prepared by subcloning a full-length DNA of the VEGF-E gene fused with a histidine tag at its carboxyl terminus into pUC18, was cleaved with a restriction enzyme. A fragment (3 kb) that was obtained by cleaving with DraIII and EcoRI and a fragment (about 3 kb) obtained by cleaving with PflMI and BamHI were purified by the gene clean method. Also, 6 oligonucleotides were produced and purified by HPLC (Amersham Pharmacia Biotech (Tokyo)):

```
S155:
5'-GTGCGAATGCC-3'                                               (SEQ ID NO:1)

S156:
5'-CATTCGCACTTT-3'                                              (SEQ ID NO:2)

S150:
5'-GGCCTCTGCGGGAGAAGATGAAGCCGGAAAGGTGCGGCGATGCTGTTCCCCGGAG     (SEQ ID NO:3)

GCACCATCACCATCACCATTAAG-3'

S151:
5'-AATTCTTAATGGTGATGGTGGATGGTGCCTCCGGGGAACAGCATCGCCGCACCTTTC  (SEQ ID NO:4)

CGGCTTCATCTTCTCCCGCAGAGGCCGG-3'
```

-continued

```
S166:
5'-GATCCATGCCGGTCATGAGGCTGTTCCCTTGCTTCCTGCAGCTCCTGGCCGGGCTGG  (SEQ ID NO:5)

CGCTGCCTGCTGTGCCCCCCCAGCAGTGGGCCTTGTCTGCTGGGAACGGCTCGTCAGA

GGTGGAAGTGAATGA-3'

S167:
5'-TTCACTTCCACCTCTGACGAGCCGTTCCCAGCAGACAAGGCCCACTGCTGGGGGGG  (SEQ ID NO:6)

CACACGAGGCAGCGCCAGCCCGGCCAGGAGCTGCAGGAAGCAAGGGAACAGCCTCA

TGACCGGCATG-3'
```

S150 and S151, S155 and S156, and S166 and S167 (10 μg/ml each) were boiled under conditions of 10 mM Tris-HCl (pH 7.5), 10 mM $MgCl_2$, 1 mM DTT, and 100 mM NaCl for 10 minutes, and then allowed to stand at room temperature for annealing. Subsequently, a DNA fragment comprising VEGF-E purified by the gene clean method and the annealed oligonucleotides were ligated to each other by DNA ligase, followed by molecular cloning on the plasmid vector. The DNA fragment of DraIII/EcoRI and oligonucleotides of S150/S151 and S155/S156 were ligated for VEGF-E-CP by DNA ligase. The DNA fragment of PflMI/BamHI and oligonucleotides of S166/S167 were ligated for VEGF-E-NP by DNA ligase. Thus, a histidine tag was fused to the carboxyl terminus. The full-length DNAs which encoded VEGF-E-CP and VEGF-E-NP were subcloned into the pUC18 plasmid vector. The plasmids were respectively designated as pUCE-CP and pUCE-NP.

(VEGF-E-NP/CP)

pUCE-CP and pUCE-NP were cleaved with BsrGI and EcoRI and 200 bp and 3 kb DNA fragments respectively obtained therefrom were purified by the gene clean method, followed by ligation with DNA ligase. Thus, a histidine tag was fused to the carboxyl terminus. The full-length DNA which encoded the VEGF-E-NP/CP was subcloned into pUC18, and this plasmid DNA was designated as pUCE-NP/CP.

Subsequently, each of the subcloned DNAs was cleaved out and subcloned into a baculovirus vector. Each DNA of pUCE-CP, pUCE-NP and pUCE-NP/CP was cleaved with BamHI and EcoRI, and 450 bp fragments were purified by the gene clean method. The fragments were cloned into the BamFHI and EcoRI site in the multicloning sites of pVL1393 (Invitrogen) which is a baculovirus vector. These plasmid DNAs were designated as pVL3E-CP, pVL3E-NP, and pVL3E-NP/CP.

Example 3

Preparation of VEGF-E Chimera Protein

By using DNAs of pVL3E-CP, pVL3E-NP and pVL3E-NP/CP and Baculogold (Pharmingen, San Diego, Calif.) of baculovirus DNA, transfection into Sf9 cells was performed by lipofectin method. Recombinant viruses having DNA encoding the chimera protein were amplified by repeating incubation for 3 to 4 days. In order to express the chimera protein, infection with the recombinant virus Sf9 cells was carried out at the multiplicity of infection (MOI) (i.e., the number of virus particles per cell) of 10. After the incubation for 3 days, a culture solution to which the chimera protein had been secreted was collected.

Subsequently, the culture solution was concentrated. In order to concentrate 150 ml of culture solution to 15 ml, an agitation-type ultrafilter device (MILLIPORE, USA) was used. The concentrate was subjected to dialysis in 20 mM sodium phosphate buffer (pH 8.0), 10 mM imidazole, 300 mM NaCl, and 20% glycerol in order to negatively charge the histidine tag that was fused with the recombinant protein.

Figure 3:
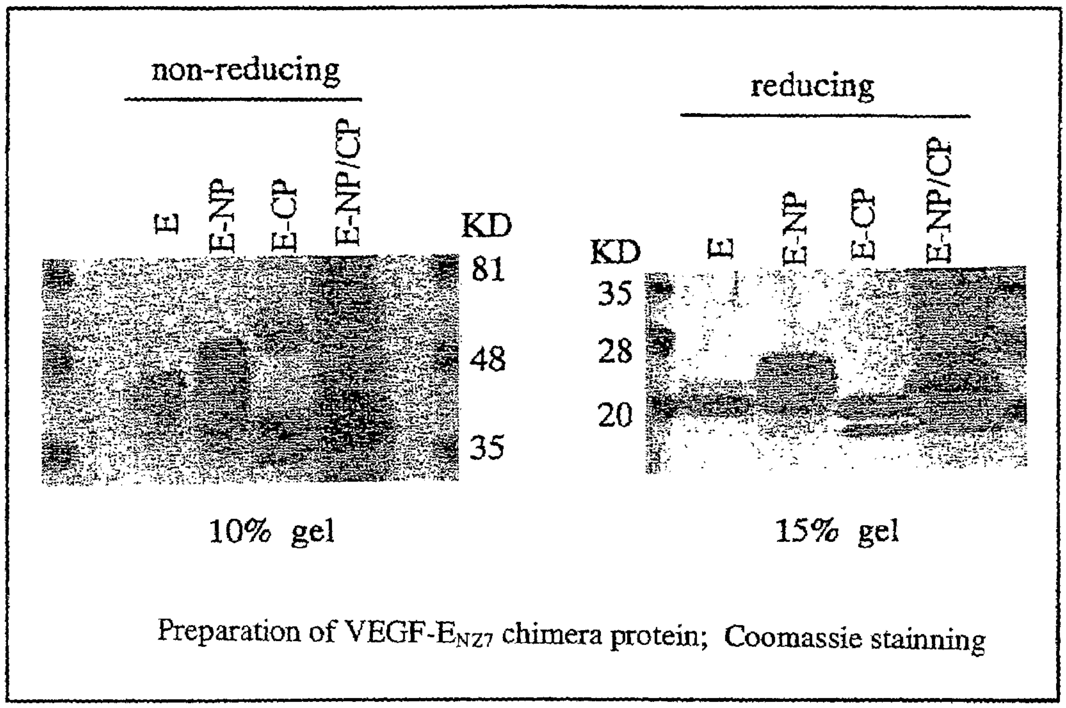
FIG. 3 shows the preparation of VEGF-$E_{N27}$ chimera protein.

After the dialysis, the histidine tag-fused protein was specifically adsorbed using Ni-NTA agarose (QIAGEN, Germany). The Ni-NTA agarose to which the recombinant protein had been adsorbed was introduced into a column and washed with 20 mM sodium phosphate buffer (pH 8.0), 50 mM imidazole, 300 mM NaCL and 20% glycerol, and the chimera protein of interest was eluted using 20 mM sodium phosphate buffer (pH 8.0), 250 mM imidazole, 300 mM NaCl, and 20% glycerol. Finally, the eluate was subjected to dialysis in 20 mM sodium phosphate buffer (pH 7.4), 50 mM NaCl, and 20% glycerol. The purified chimera protein was electrophoresed in 15% SDS-PAGE and analyzed by Coomassie staining and Western blotting using anti-histidine tag monoclonal antibody (anti-His-tagmAb), anti-VEGF-E serum, and anti-PIGF antibody. The purification level of the chimera protein was 80% or higher (FIG. 3).

Example 4

Experiment on Competitive Inhibition of VEGF-E Chimera Protein on KDR Receptor Fc-fused 7N-sKDR was diluted to 3 μg/ml in physiological saline (hereinafter abbreviated to "PBS"), 50 μl thereof was added to each well of a 96-well cell culture plate (Immunon (registered trademark) 2HB, DYNEX TECHNOLOGIES, INC, VA), allowed to stand at 4° C. for 12 hours, and $_s$KDR was then adsorbed on the plate. The plate was washed twice with a blocking buffer (PBS containing 1% bovine serum albumin), and blocking was carried out using the blocking buffer at 25° C. for 30 minutes. In the experiment on competitive inhibition, 50 μl of sample containing 16 μg/ml of $^{125}$I-radioactively labeled VEGF (1,200-1,800 Ci/mmol; Amersham Pharmacia Biotech) and 16-1,000 μg/ml of chimera protein was added to the $_s$KDR-coated wells, a reaction was carried out at 25° C. for 3 hours, and the wells were then washed with a blocking buffer. The $^{125}$I-radioactively labeled VEGF bound to $_s$KDR of each well was assayed using a γ-counter.

Figure 4:
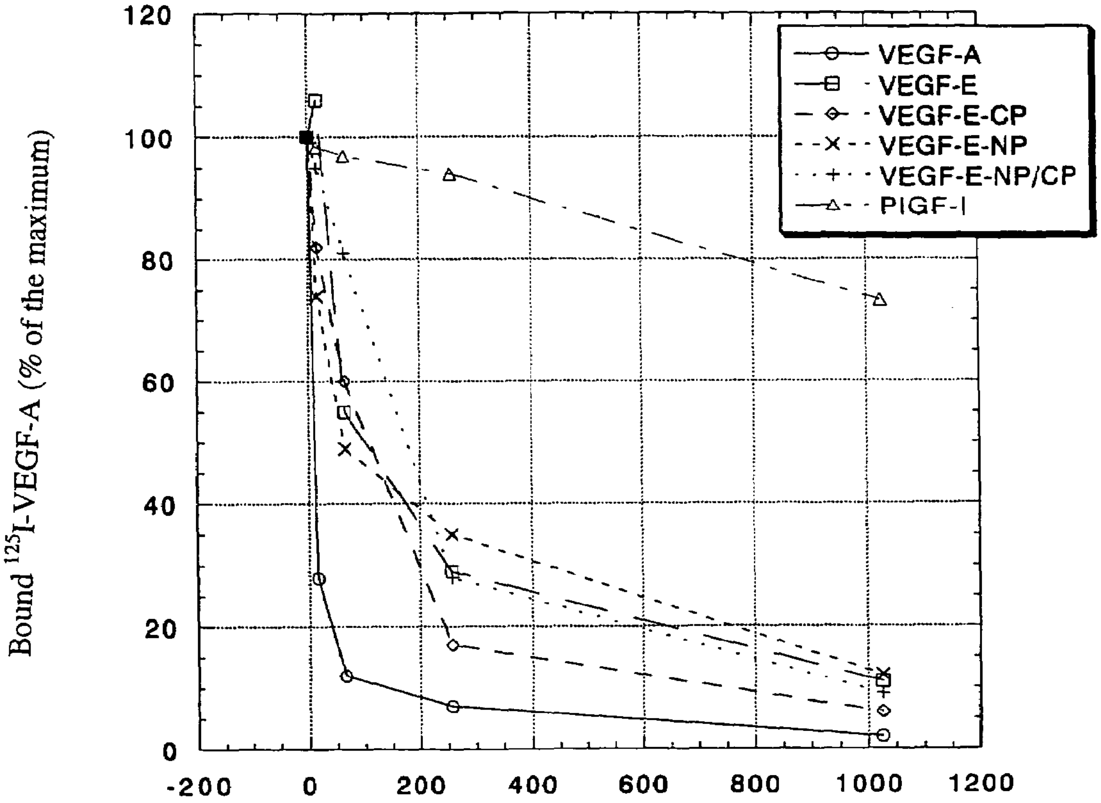
FIG. 4 shows the result of the experiment for competitive inhibition of VEGF-$E_{N27}$ chimera protein on the KDR receptor.

The results showed that the three types of chimera VEGF-$E_{N27}$ proteins (VEGF-E-NP, VEGF-E-CP, VEGF-E-NP/CP) efficiently inhibited the binding of VEGF to KDR. This strongly indicates that the chimera VEGF-$E_{N27}$ protein binds to KDR with high affinity (FIG. 4).

Example 5

Experiment for Assaying Autophosphorylation of KDR Receptor

In order to confirm that the chimera VEGF-EN$2_7$ proteins directly bind to and activate KDR, an experiment was carried out to assay the autophosphorylation of the KDR receptor by these proteins. Before the NIH3T3-KDR cells were stimulated with the chimera proteins, the cells were cultured until 60% confluent. Thereafter, the cells were exposed to low-concentration serum conditions in DMEM containing 0.5% bovine serum overnight. The cells were stimulated by each of the chimera proteins at a concentration of 1 to 500 ng/ml at 37° C. for 5 minutes. The cells were washed twice in ice-cooled PBS containing 0.1 mM $Na_3VO_4$, and then dissolved with a 1% Triton X-100 buffer solution (50 mM HEPES pH 7.4, 150 mM NaCl, 10% glycerol, 1% Triton X-100, 1.5 mM MgCl, 2% trasylol, 1 mM PMSF, 50 mM NaF, 10 mM $Na_4P_2O_7$, 2 mM $Na_3VO_4$). The dissolved sample was centrifuged at 15,000 rpm for 10 minutes, and the supernatant was collected. The protein concentration in the supernatant was assayed using the Bio-Rad Protein Assay Kit (Richmond, Calif.), and an equivalent protein was used in the analysis. In the immunoblotting for analyzing the autophosphorylated KDR, the dissolved sample was electrophoresed in 7.5% SDS-PAGE and then transferred to a nitrocellulose membrane. The transferred nitrocellulose membrane was blocked with a blocking buffer (a washing buffer containing 5% BSA [20 mM Tris-HCl, pH 7.4, 150 mM NaCl, 0.1% Tween 20]), and binding reaction was then carried out with a blocking buffer containing a primary antibody.

Signals obtained by Western blotting were analyzed using horseradish peroxidase-conjugated secondary antibodies and enhanced chemiluminescence reagents (EC, Amersham).

Figure 5:
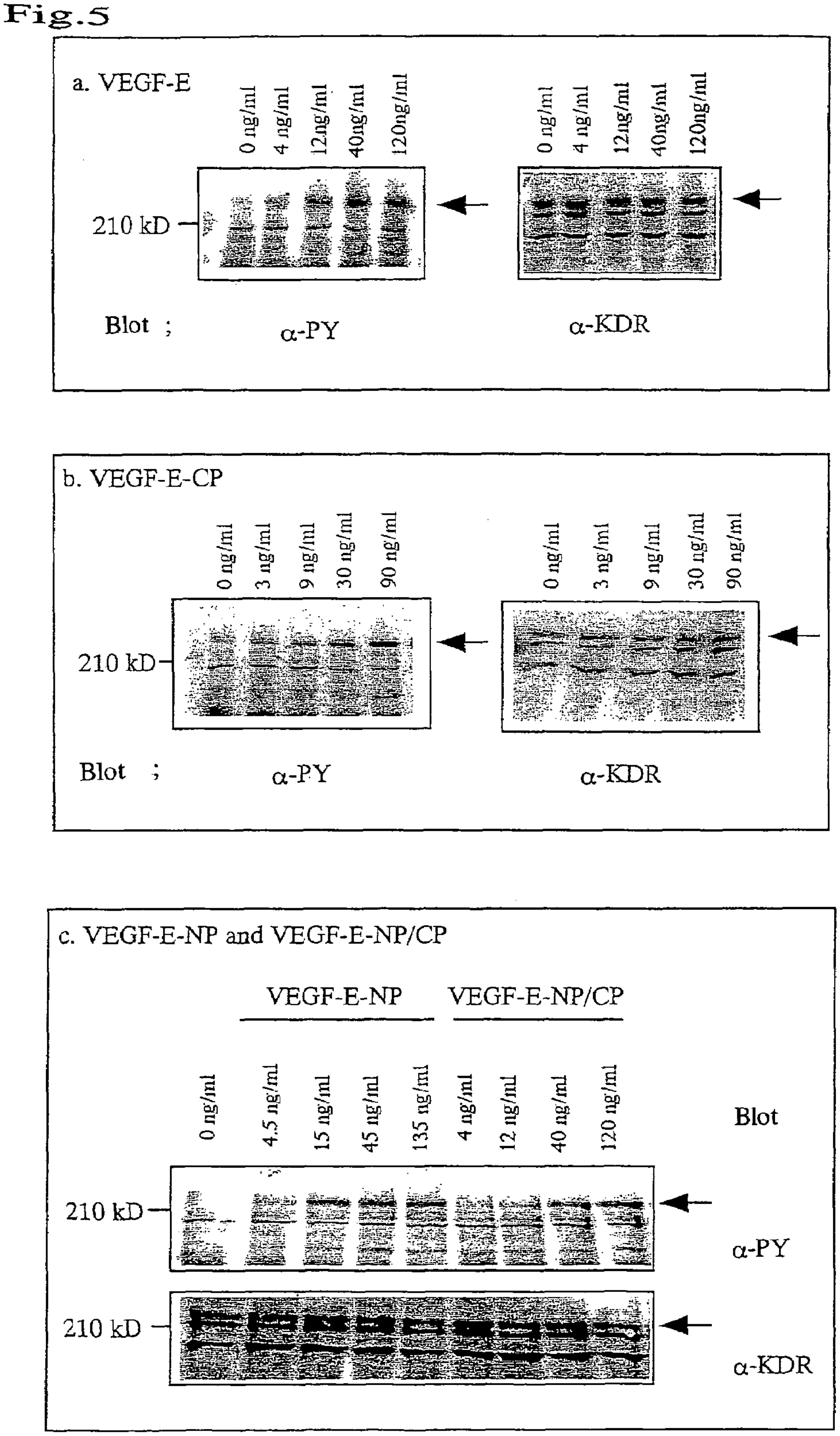
FIG. 5 shows the result of the experiment for assaying the autophosphorylation of KDR receptor.

As a result, the three types of chimera VEGF-$E_{N27}$ proteins (VEGF-E-NP, VEGF-E-CP, VEGF-E-NP/CP) were found to activate the tyrosine kinase of the KDR receptor in a dosage-dependent manner (FIG. 5).

Example 6

Experiment for Vascular Endothelial Cell Growth

Figure 6:
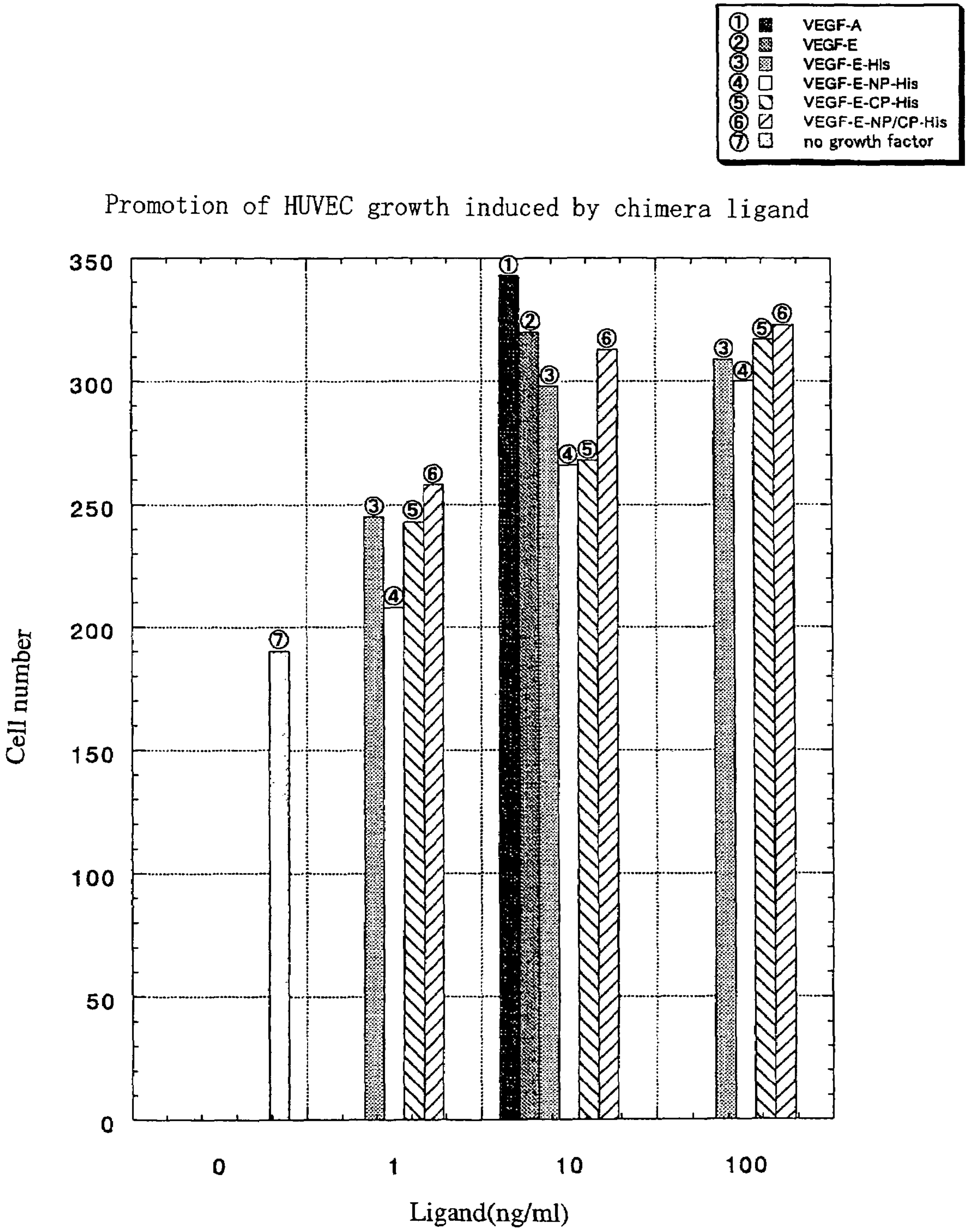
FIG. 6 shows the result of the experiment on vascular endothelial cell growth.

The HUVEC (Morinaga, Tokyo) which were cultured in the medium for HUVE culture (Nissui) containing growth factors, FGF, added thereto, were inoculated on a 24-well plate (CellTite C-1 Plate 24F, Akita Sumitomo Bakelite Co., Ltd., Akita) in amounts of 4,000 cells, and allowed to stand in an incubator at 37° C. for 4 hours to adsorb the cells. The chimera VEGF-E protein was directly added to the medium to a final concentration of 50 ng/ml, and cultured for 3 days. The cells were fixed with formalin and then stained with Crystal Violet The number of cells was counted and relatively compared to analyze the endothelial cell growth. The results showed that the chimera protein had the equivalent activity of endothelial cell growth as the VEGF-E protein in vitro (FIG. 6).

Summary of Examples 1 to 6

From the above results, the three types of chimera VEGF-$E_{N27}$ proteins (VEGF-E-NP, VEGF-E-CP, VEGF-E-NP/CP) were found to bind to KDR with high affinity, accelerate the autophosphorylation of KDR, and stimulate the vascular endothelial cell growth. The antigenicity of the protein is known to be relatively strong at free termini such as an amino or carboxyl terminus, however, both termini of VEGF-E were found to be unnecessary for activating KDR tyrosine kinase and could be substituted with a human-derived protein such as PIGF used in the Example. Accordingly, these chimera VEGF-$E_{N27}$ proteins (VEGF-E-NP, VEGF-E-CP, VEGF-E-NP/CP) are considered to be usable as safer vascularization factors than the original VEGF-$E_{N27}$ proteins.

Example 7

Production of Chimera VEGF-E Proteins (#19 to #27 and #31 to #33)

(1) Production of Chimera VEGF-E Proteins #19 to #27

Figure 12:
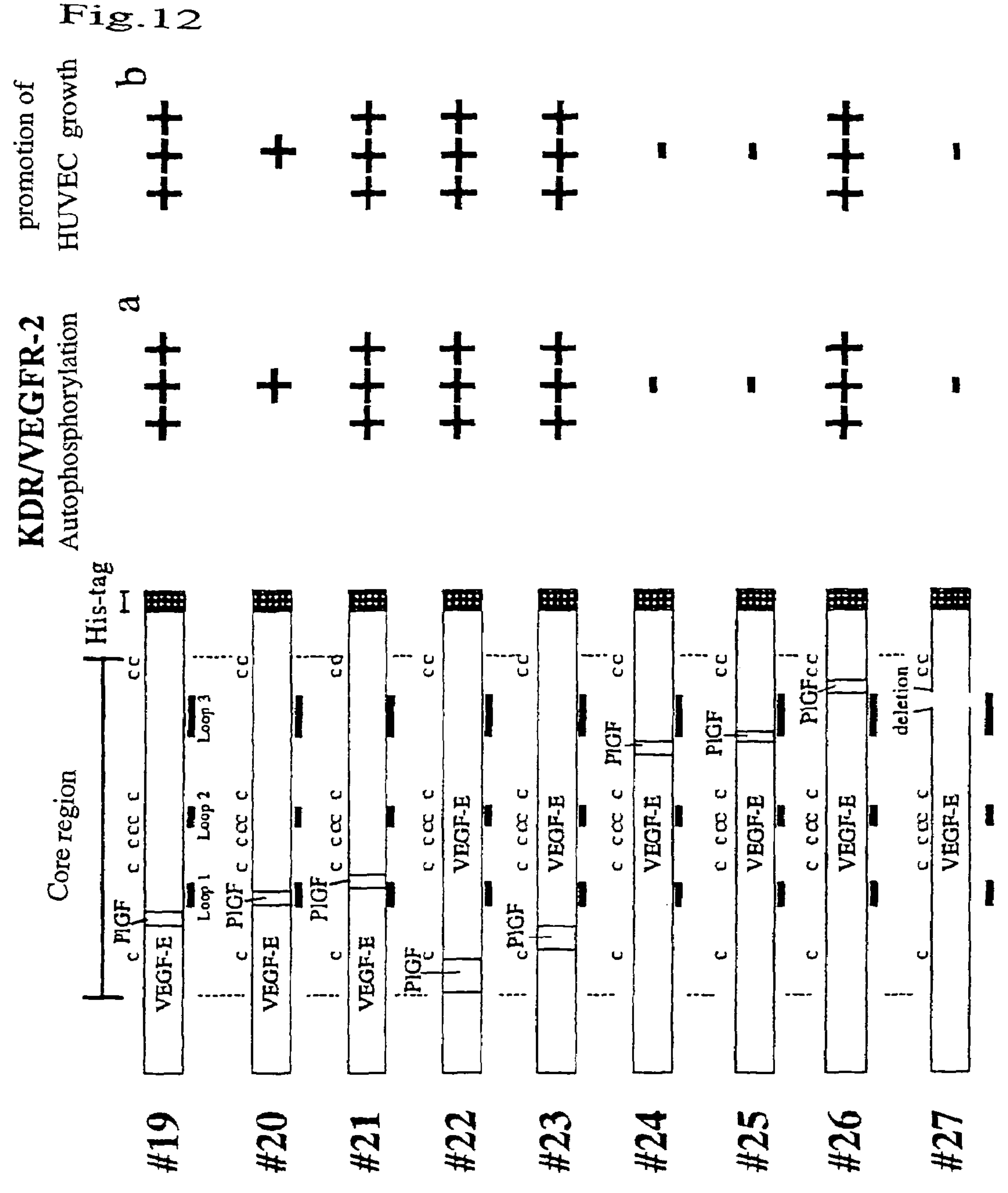
FIG. 12 shows the structures of VEGF-E chimera proteins #19 to #27 and a summary of the results of the experiment for assaying the autophosphorylation of the KDR receptor and the experiment on vascular endothelial cell growth.

The amino acid sequence of the substituted region is shown below. The nucleotide sequence of PIGF was used for that of the substituted region. Structures of the chimera VEGF-E proteins #19 to #27 are shown in FIG. 12.

#19: the amino acid sequence from residues #54-57 (YLGE) of VEGF-E (SEQ ID NO: 7) is substituted with the amino acid sequence (DVVS) (SEQ ID NO: 21) of the corresponding region in human PIGF.

#20: the amino acid sequence from residues #62-64 (STN) of VEGF-E (SEQ ID NO: 7) is substituted with the amino acid sequence (EVE) of the corresponding region in human PIGF.

#21: the amino acid sequence from residues #65-68 (LQYN) of VEGF-E (SEQ ID NO: 7) is substituted with the amino acid sequence (HMFS) (SEQ ID NO: 22) of the corresponding region in human PIGF.

#22: the amino acid sequence from residues #3743 (WMRTLDK) of VEGF-E (SEQ ID NO: 7) is substituted with the amino acid sequence (FQEVWGR) (SEQ ID NO: 23) of the corresponding region in human PIGF.

#23: the amino acid sequence from residues #47-52 (KPRDTV) (β chain #1) of VEGF-E (SEQ ID NO: 7) is substituted with the amino acid sequence (RALERL) (SEQ ID NO: 24) of the corresponding region in human PIGF.

#24: the amino acid sequence from residues #98-101 (VTVS) (β chain #6, between cysteine 6 and cysteine 7) of VEGF-E (SEQ ID NO: 7) is substituted with the amino acid sequence (MQLL) (SEQ ID NO: 26) of the corresponding region in human PIGF.

#25: the amino acid sequence from residues #102-104 (VTG) (a portion of loop 3) of VEGF-E (SEQ ID NO: 7) is substituted with the amino acid sequence (KTR) of the corresponding region in human PIGF.

#26: the amino acid sequence from residues #119-122 (LQRI) (β chain #7, 11 amino acid residues upstream region from the 7th cysteine) of VEGF-E (SEQ ID NO: 7) is substituted with the amino acid sequence (YVEL) (SEQ ID NO: 25) of the corresponding region in human PIGF.

#27: the amino acid sequence from residues #111-118 (TNSGVSTN) (VEGF-E-specific amino acid sequence) of VEGF-E (SEQ ID NO: 7) is removed (deletion mutation).

(2) Production of Chimera VEGF-E Proteins #31 to #33

Figure 15:
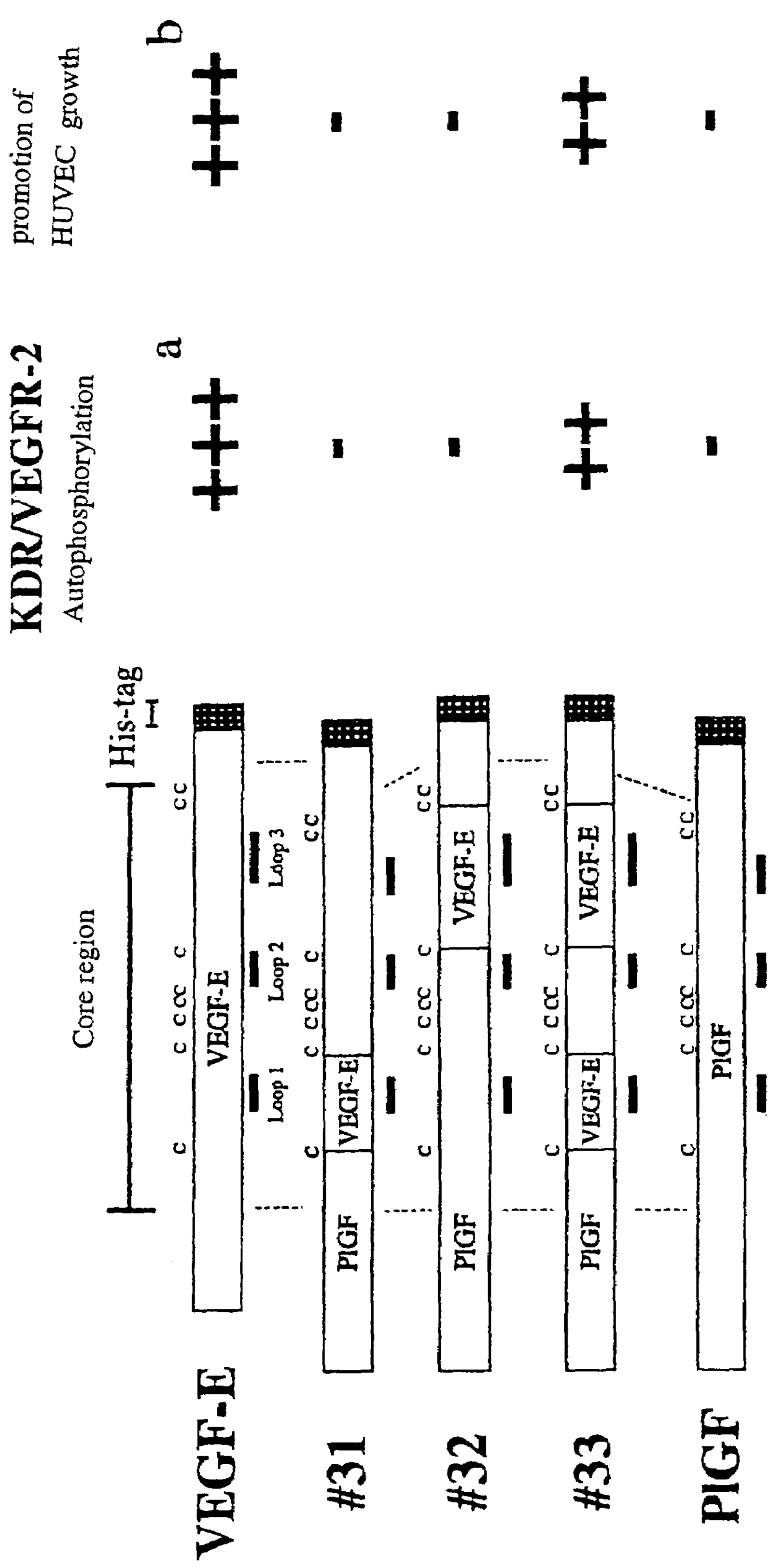
FIG. 15 shows the structures of VEGF-E chimera proteins #31 to #33 and a summary of the results of the experiment for assaying the autophosphorylation of the KDR receptor and the experiment on vascular endothelial cell growth.

The structures of the chimera proteins are shown below as nucleotide sequences. The structures of chimera VEGF-E proteins #31 to #33 are shown in FIG. 15.

Boxed portions: cysteine sites (the 2nd, 3rd, 4th, and 5th)

Underlined portions: VEGF-E sequences

Fundamental nucleotide sequence: PIGF-I

#31 (SEQ ID NO: 12): the amino acid sequence between the 2nd cysteine and the 3rd cysteine of human PIGF is substituted with the corresponding amino acid sequence of VEGF-E atgccggtcatgaggctgttcccttgcttcctgcagctcctggccgggctggcgctgcctgctgtgcccccccagcagtgggccttgtctgctggg aacggctcgtcagaggtggaagtggtacccttccaggaagtgtggggccgcagctactgcaaacctagagatactgttgtttatttgggagaaga atatccagaaagcactaacctacaatataatccccggtgtgtctccctgctgcgctgcaccggctgctgcggcgatgagaatctgcactgtgtgcc ggtggagacggccaatgtcaccatgcagctcctaaageatccgttctggggaccggccctcctacgtggagctgacgttctctcagcacgttcgct gcgaatgccggcctctgcgggagaagatgaagccggaaaggtgcggc gatgctgttccccggaggtaa

Figure 14:
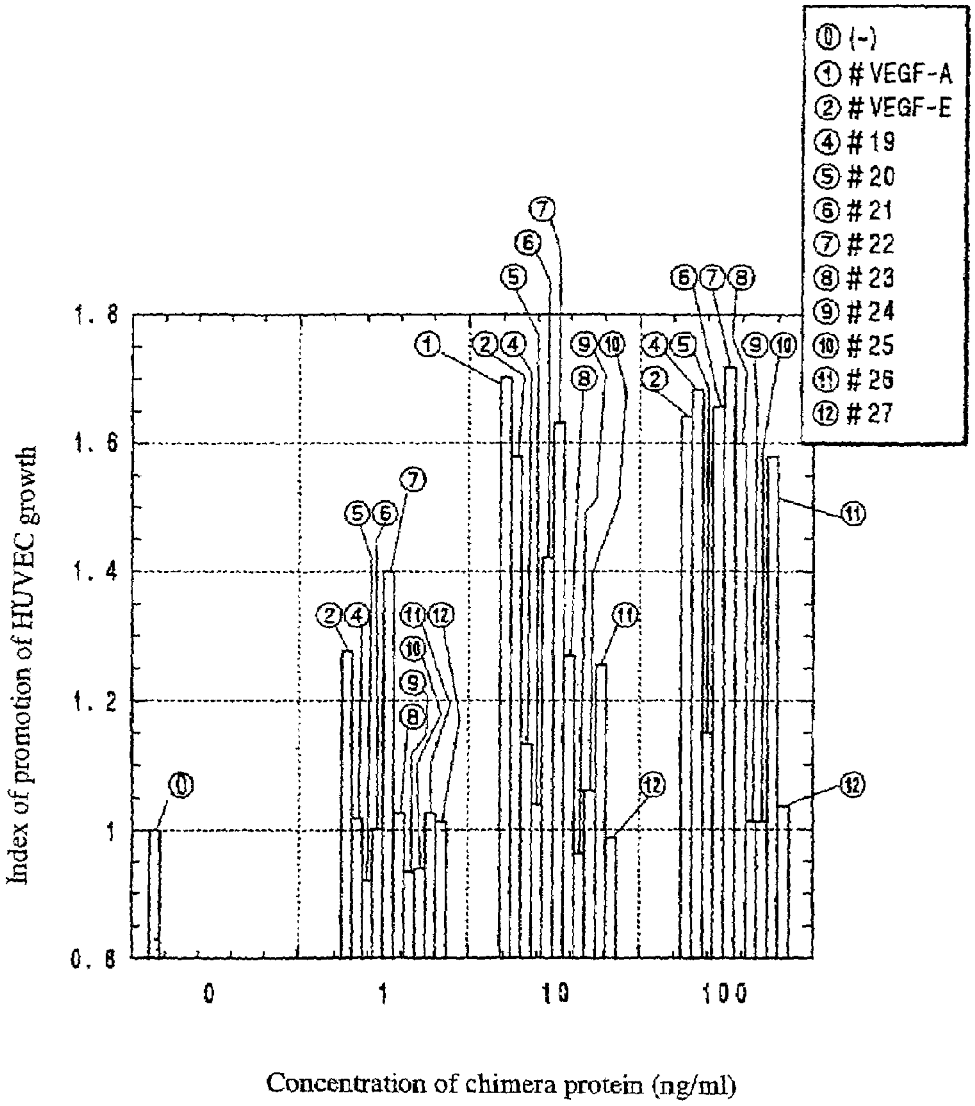
FIG. 14 shows the results of the experiment on vascular endothelial cell growth using the VEGF-E chimera proteins #19 to #27.

#32 (SEQ ID NO: 13): the amino acid sequence between the 4th cysteine and the 5th cysteine of human PIGF is substituted with the corresponding amino acid sequence of VEGF-E shows the assay result obtained by the experiment on competitive inhibition on KDR receptor. FIG. 14 shows the assay result obtained by the experiment on vascular endothelial cell growth.

atgccggtcatgaggctgttcccttgcttcctgcagctcctggccgggctggcgctgcctgctgtgcccccccagcagtgggccttgtctgctggg aacggctcgtcagaggtggaagtggtacccttccaggaagtgtggggccgcagctactgccgggcgctggagaggctggtggacgtcgtgtc cgagtaccccagcgaggtggagcacatgttcagcccatcctgtgtctccctgctgcgctgcaccggctgctgcggcgatgagaatctgcactgt acagcggttgaaacaagaaatacaactgtaacagtttcagtaaccggcgtgtctagttcgtctggtactaatagtggtgtatctactaaccttcaaag aataagtgttacagaacacacaaagtgcgaatgccggcctctgcgggagaagatgaagccggaaaggtgcggcgatgctgttccccggaggt aa

Figure 16:
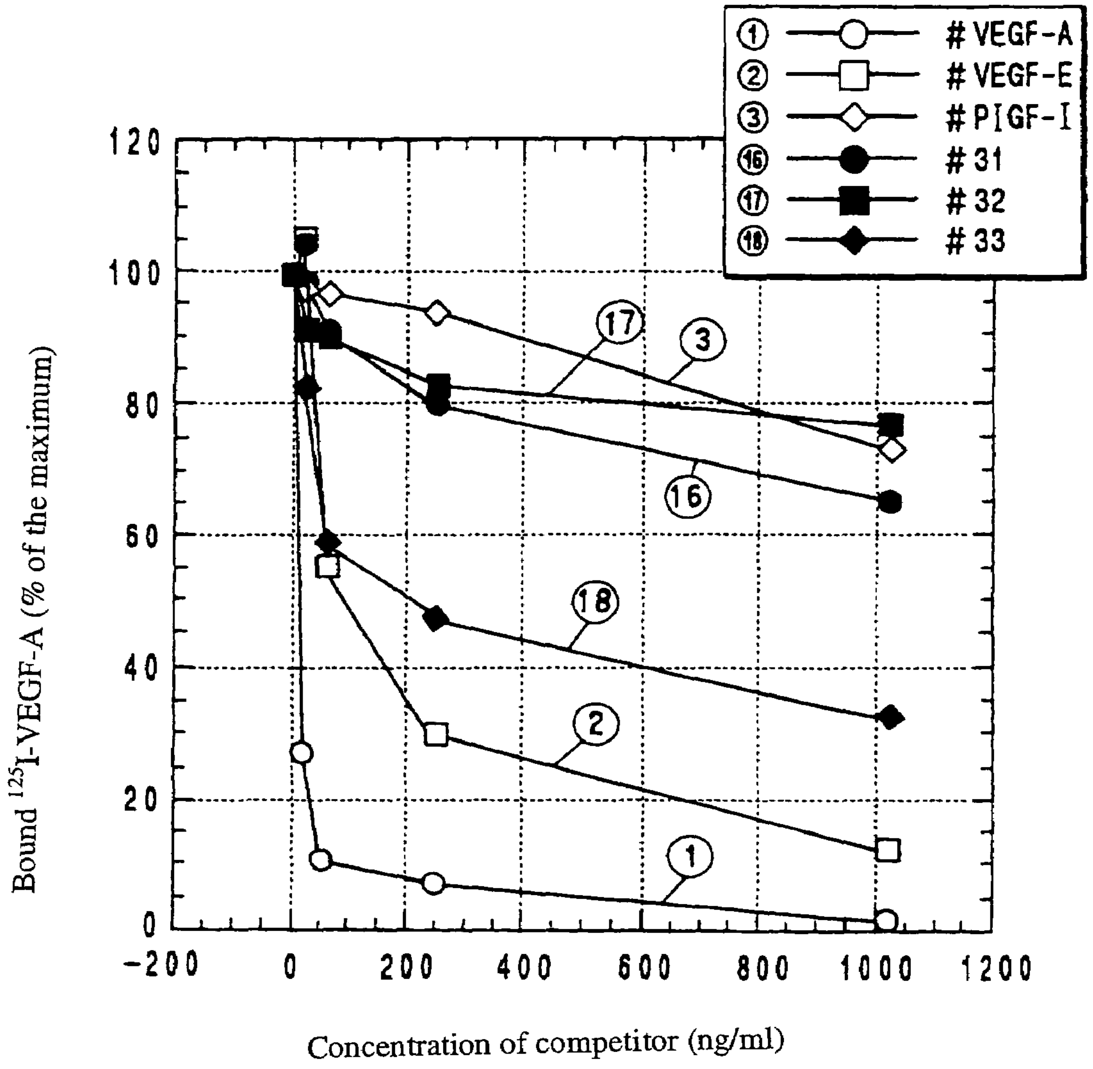
FIG. 16 shows the results of the experiment on competitive inhibition on the KDR receptor using the VEGF-E chimera proteins #31 to #33.

#33 (SEQ ID NO: 14): the amino acid sequence between the 2nd cysteine and the 3th cysteine and the amino acid sequence between the 4th cysteine and the 5th cysteine of human PIGF are substituted with the corresponding amino acid sequences of VEGF-E FIG. 15 shows the structures of VEGF-E chimera proteins #31 to #33 and a summary of the results of the experiment for assaying the autophosphorylation of KDR receptor and the experiment of vascular endothelial cell growth. FIG. 16 shows the assay result obtained by the experiment on comatgccggtcatgaggctgttcccttgcttcctgcagctcctggccgggctggcgctgcctgctgtgcccccccagcagtgggccttgtctgctggg aacggctcgtcagaggtggaagtggtacccttccaggaagtgtggggccgcagctactgcaaacctagagatactgttgtttatttgggagaaga atatccagaaagcactaacctacaatataatccccggtgtgtctccctgctgcgctgcaccggctgctgcggcgatgagaatctgcactgtacag cggttgaaacaagaaatacaactgtaacagtttcagtaaccggcgtgtctagttcgtctggtactaatagtggtgtatctactaaccttcaaagaataa gtgttacagaacacacaaagtgcgaatgccggcctctgcgggagaagatgaagccggaaaggtgcggcgatgctgttccccggaggtaa DNA fragments having the above sequences were constructed by conventional gene recombinant techniques, and VEGF-E chimera proteins (#19 to #27 and #31 to #33) were prepared in the same manner as in Example 3.

Example 8

Physiological Activities of Chimera VEGF-E Proteins (#19 to #27 and #31 to #33)

The VEGF-E chimera proteins (#19 to #27 and #31 to #33) prepared in Example 7 were used to perform an experiment on competitive inhibition on the KDR receptor (in the same manner as in Example 4), an experiment for assaying autophosphorylation of the KDR receptor (in the same manner as in Example 5), and an experiment on vascular endothelial cell growth (in the same manner as in Example 6).

Figure 13:
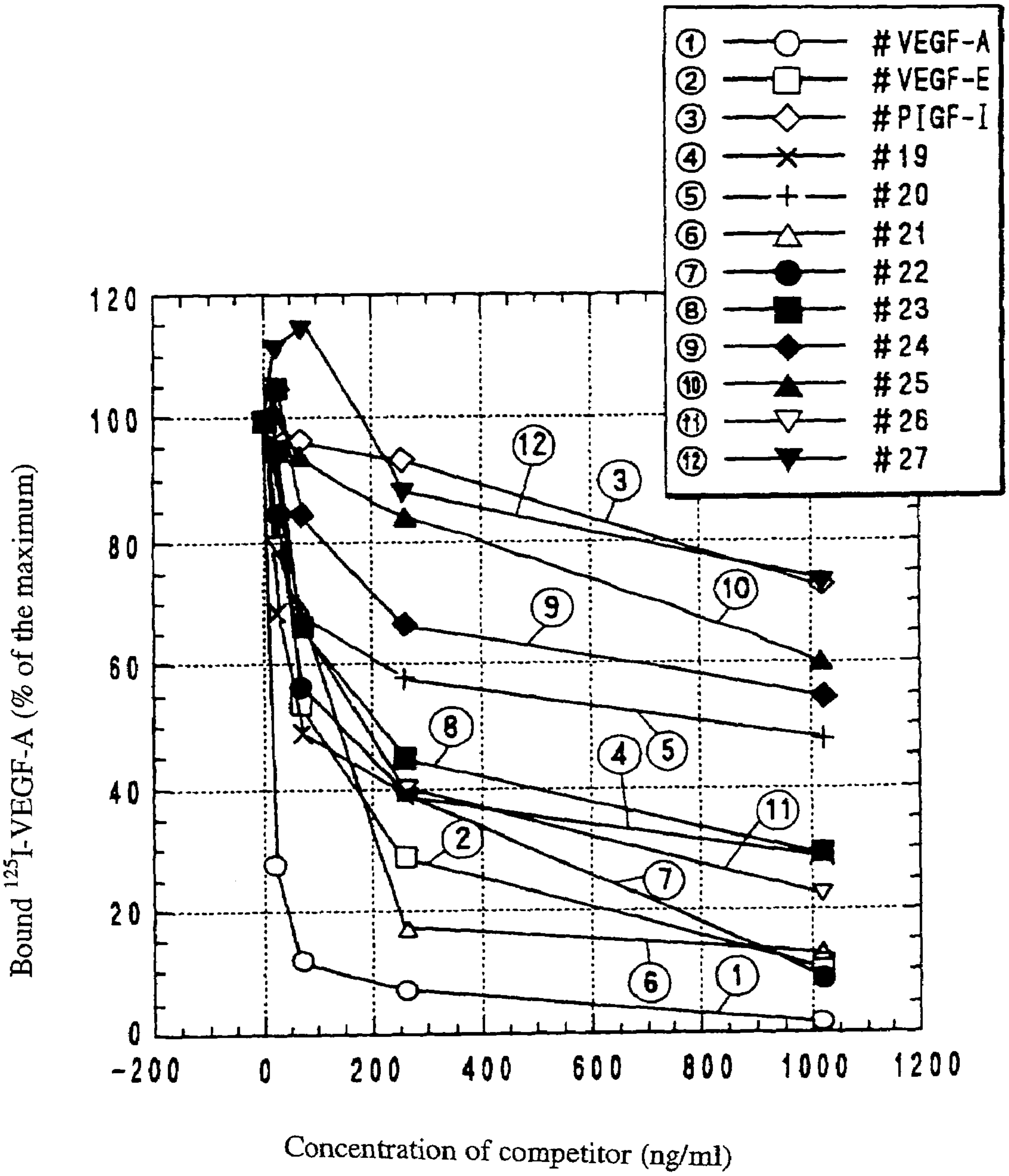
FIG. 13 shows the results of the experiment on competitive inhibition on the KDR receptor using the VEGF-E chimera proteins #19 to #27.
Figure 17:
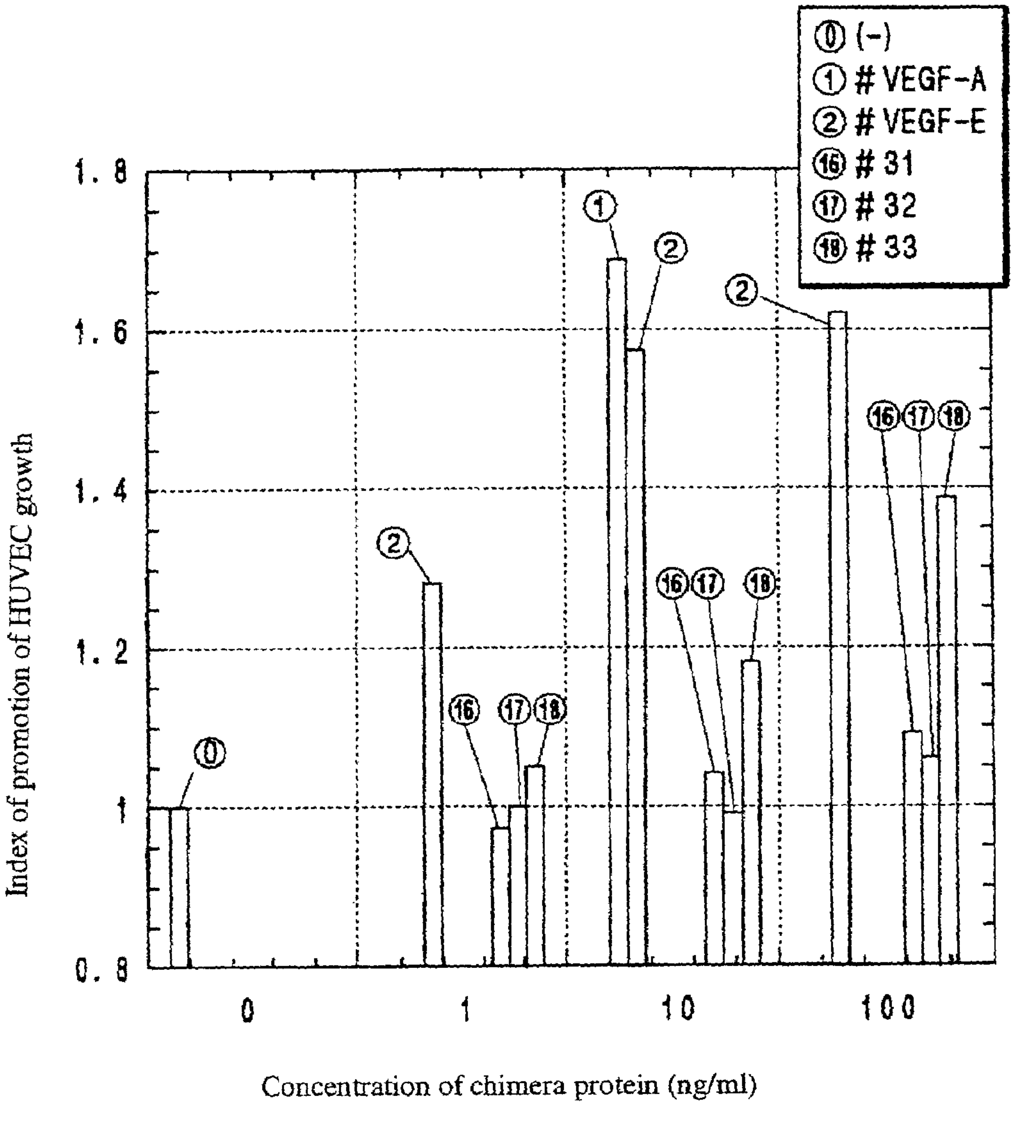
FIG. 17 shows the results of the experiment on vascular endothelial cell growth using the VEGF-E chimera proteins #31 to #33.

FIG. 12 shows the structures of VEGF-E chimera proteins #19 to #27 and summarized results of the experiment for assaying the autophosphorylation of the KDR receptor and the experiment on vascular endothelial cell growth. FIG. 13 petitive inhibition on KDR receptor. FIG. 17 shows the assay result obtained by the experiment on vascular endothelial cell growth.

As is apparent from the results shown in FIGS. 12 to 14, it was found that all the chimera proteins other than #24, #25, and #27 bind to KDR with high affinity, accelerate the autophosphorylation of KDR, and stimulate the growth of vascular endothelial cells. Accordingly, it was clarified that not only both termini of VEGF-E but also some internal sequences in VEGF-E can be substituted with human-derived protein such as PIGF.

As is apparent from the results shown in FIGS. 15 to 17, it was found that #33, which was obtained by substituting the amino acid sequence between the 2nd cysteine and the 3rd cysteine in human PIGF that exhibits no autophosphorylation of KDR receptor and no vascular endothelial cell growth (including loop 1 in the core region of human PIGF) and the amino acid sequence between the 4th cysteine and the 5th cysteine (including loop 3 in the core region of human PIGF)

with the corresponding amino acid sequences of VEGF-E (respectively including loop 1 and loop 3 in the core region of VEGF-E), accelerates the autophosphorylation of KDR and stimulates the growth of vascular endothelial cells. Accordingly, loop 1 and loop 3 in the core region possibly play a role in the expression of physiological activities of VEGF-E.

INDUSTRIAL APPLICABILITY

The chimera VEGF-E of the present invention can be used as a safe vascularization factor since its antigenicity is reduced while maintaining the activity of growing vascular endothelial cells.

The invention claimed is:

1. A chimera protein which has any of the amino acid sequences shown below:

(A) the amino acid sequence as shown in SEQ ID NO 15; or (B) the amino acid sequence as shown in SEQ ID NO: 15, in which one to ten amino acids are deleted, substituted, and/or added, and which has an activity of growing vascular endothelial cells.

2. A chimera protein having the amino acid sequence of SEQ ID NO: 15, in which one to five amino acids are deleted, substituted, and/or added, and which has an activity of growing vascular endothelial cells.

* * * * *

SEQUENCE LISTING

```
<160> NUMBER OF SEQ ID NOS: 15

<210> SEQ ID NO 1
<211> LENGTH: 11
<212> TYPE: DNA
<213> ORGANISM: Artificial
<220> FEATURE:
<223> OTHER INFORMATION: Primer

<400> SEQUENCE: 1

gtgcgaatgc c                                                            11


<210> SEQ ID NO 2
<211> LENGTH: 12
<212> TYPE: DNA
<213> ORGANISM: Artificial
<220> FEATURE:
<223> OTHER INFORMATION: Primer

<400> SEQUENCE: 2

cattcgcact tt                                                           12


<210> SEQ ID NO 3
<211> LENGTH: 78
<212> TYPE: DNA
<213> ORGANISM: Artificial
<220> FEATURE:
<223> OTHER INFORMATION: Primer

<400> SEQUENCE: 3

ggcctctgcg ggagaagatg aagccggaaa ggtgcggcga tgctgttccc cggaggcacc      60

atcaccatca ccattaag                                                     78


<210> SEQ ID NO 4
<211> LENGTH: 85
<212> TYPE: DNA
<213> ORGANISM: Artificial
<220> FEATURE:
<223> OTHER INFORMATION: Primer

<400> SEQUENCE: 4

aattcttaat ggtgatggtg gatggtgcct ccggggaaca gcatcgccgc acctttccgg      60

cttcatcttc tcccgcagag gccgg                                             85


<210> SEQ ID NO 5
<211> LENGTH: 130
<212> TYPE: DNA
<213> ORGANISM: Artificial
<220> FEATURE:
<223> OTHER INFORMATION: Primer

<400> SEQUENCE: 5

gatccatgcc ggtcatgagg ctgttccctt gcttcctgca gctcctggcc gggctggcgc      60

tgcctgctgt gcccccccag cagtgggcct tgtctgctgg gaacggctcg tcagaggtgg     120
```

-continued

```
aagtgaatga                                                          130

<210> SEQ ID NO 6
<211> LENGTH: 123
<212> TYPE: DNA
<213> ORGANISM: Artificial
<220> FEATURE:
<223> OTHER INFORMATION: Primer

<400> SEQUENCE: 6

ttcacttcca cctctgacga gccgttccca gcagacaagg cccactgctg ggggggcaca     60

cgaggcagcg ccagcccggc caggagctgc aggaagcaag ggaacagcct catgaccggc    120

atg                                                                  123

<210> SEQ ID NO 7
<211> LENGTH: 465
<212> TYPE: DNA
<213> ORGANISM: Artificial
<220> FEATURE:
<223> OTHER INFORMATION: Sequence encoding Chimeric VEGF protein

<400> SEQUENCE: 7

atgaagttaa cagctacgtt acaagttgtt gttgcattgt taatatgtat gtataatttg     60

ccagaatgcg tgtctcagag taatgattca cctccttcaa ccaatgactg gatgcgtaca    120

ctagacaaaa gtggttgtaa acctagagat actgttgttt atttgggaga agaatatcca    180

gaaagcacta acctgcagta taatccccgg tgcgtaactg ttaaacgatg cagtggttgc    240

tgtaacggtg acggtcaaat atgtacagcg gttgaaacaa gaaatacaac tgtaacagtt    300

tcagtaaccg gcgtgtctag ttcgtctggt accaatagtg gtgtatctac taaccttcaa    360

agaataagtg ttacagaaca cacaaagtgc gattgtattg gtagaacaac gacaacacct    420

acgaccacta gggaacctag acgacaccat caccatcacc attaa                    465

<210> SEQ ID NO 8
<211> LENGTH: 483
<212> TYPE: DNA
<213> ORGANISM: Artificial
<220> FEATURE:
<223> OTHER INFORMATION: Sequence encoding Chimeric VEGF protein

<400> SEQUENCE: 8

atgccggtca tgaggctgtt cccttgcttc ctgcagctcc tggccgggct ggcgctgcct     60

gctgtgcccc cccagcagtg ggccttgtct gctgggaacg gctcgtcaga ggtggaagtg    120

aatgactgga tgcgtacact agacaaaagt ggttgtaaac ctagagatac tgttgtttat    180

ttgggagaag aatatccaga aagcactaac ctgcagtata atccccggtg cgtaactgtt    240

aaacgatgca gtggttgctg taacggtgac ggtcaaatat gtacagcggt tgaaacaaga    300

aatacaactg taacagtttc agtaaccggc gtgtctagtt cgtctggtac caatagtggt    360

gtatctacta accttcaaag aataagtgtt acagaacaca caaagtgcga ttgtattggt    420

agaacaacga caacacctac gaccactagg gaacctagac gacaccatca ccatcaccat    480

taa                                                                  483

<210> SEQ ID NO 9
<211> LENGTH: 474
<212> TYPE: DNA
<213> ORGANISM: Artificial
<220> FEATURE:
<223> OTHER INFORMATION: Sequence encoding Chimeric VEGF protein
```

-continued

<400> SEQUENCE: 9
atgaagttaa cagctacgtt acaagttgtt gttgcattgt taatatgtat gtataatttg 60
ccagaatgcg tgtctcagag taatgattca cctccttcaa ccaatgactg gatgcgtaca 120
ctagacaaaa gtggttgtaa acctagagat actgttgttt atttgggaga agaatatcca 180
gaaagcacta acctgcagta taatccccgg tgcgtaactg ttaaacgatg cagtggttgc 240
tgtaacggtg acggtcaaat atgtacagcg gttgaaacaa gaaatacaac tgtaacagtt 300
tcagtaaccg gcgtgtctag ttcgtctggt accaatagtg gtgtatctac taaccttcaa 360
agaataagtg ttacagaaca cacaaagtgc gaatgccggc ctctgcggga gaagatgaag 420
ccggaaaggt gcggcgatgc tgttccccgg aggcaccatc accatcacca ttaa 474

<210> SEQ ID NO 10
<211> LENGTH: 492
<212> TYPE: DNA
<213> ORGANISM: Artificial
<220> FEATURE:
<223> OTHER INFORMATION: Sequence encoding Chimeric VEGF protein

<400> SEQUENCE: 10
atgccggtca tgaggctgtt cccttgcttc ctgcagctcc tggccgggct ggcgctgcct 60
gctgtgcccc cccagcagtg ggccttgtct gctgggaacg gctcgtcaga ggtggaagtg 120
aatgactgga tgcgtacact agacaaaagt ggttgtaaac ctagagatac tgttgtttat 180
ttgggagaag aatatccaga aagcactaac ctgcagtata atccccggtg cgtaactgtt 240
aaacgatgca gtggttgctg taacggtgac ggtcaaatat gtacagcggt tgaaacaaga 300
aatacaactg taacagtttc agtaaccggc gtgtctagtt cgtctggtac caatagtggt 360
gtatctacta accttcaaag aataagtgtt acagaacaca caaagtgcga atgccggcct 420
ctgcgggaga agatgaagcc ggaaaggtgc ggcgatgctg ttccccggag gcaccatcac 480
catcaccatt aa 492

<210> SEQ ID NO 11
<211> LENGTH: 468
<212> TYPE: DNA
<213> ORGANISM: Artificial
<220> FEATURE:
<223> OTHER INFORMATION: Sequence encoding Chimeric VEGF protein

<400> SEQUENCE: 11
atgccggtca tgaggctgtt cccttgcttc ctgcagctcc tggccgggct ggcgctgcct 60
gctgtgcccc cccagcagtg ggccttgtct gctgggaacg gctcgtcaga ggtggaagtg 120
gtacccttcc aggaagtgtg gggccgcagc tactgccggg cgctggagag gctggtggac 180
gtcgtgtccg agtaccccag cgaggtggag cacatgttca gcccatcctg tgtctccctg 240
ctgcgctgca ccggctgctg cggcgatgag aatctgcact gtgtgccggt ggagacggcc 300
aatgtcacca tgcagctcct aaagatccgt tctggggacc ggccctccta cgtggagctg 360
acgttctctc agcacgttcg ctgcgaatgc cggcctctgc gggagaagat gaagccggaa 420
aggtgcggcg atgctgttcc ccggaggcac catcaccatc accattaa 468

<210> SEQ ID NO 12
<211> LENGTH: 450
<212> TYPE: DNA
<213> ORGANISM: Artificial
<220> FEATURE:

-continued

<223> OTHER INFORMATION: Sequence encoding Chimeric VEGF protein

<400> SEQUENCE: 12

```
atgccggtca tgaggctgtt cccttgcttc ctgcagctcc tggccgggct ggcgctgcct     60
gctgtgcccc cccagcagtg ggccttgtct gctgggaacg gctcgtcaga ggtggaagtg    120
gtacccttcc aggaagtgtg gggccgcagc tactgcaaac ctagagatac tgttgtttat    180
ttgggagaag aatatccaga aagcactaac ctacaatata atccccggtg tgtctccctg    240
ctgcgctgca ccggctgctg cggcgatgag aatctgcact gtgtgccggt ggagacggcc    300
aatgtcacca tgcagctcct aaagatccgt tctggggacc ggccctccta cgtggagctg    360
acgttctctc agcacgttcg ctgcgaatgc cggcctctgc gggagaagat gaagccggaa    420
aggtgcggcg atgctgttcc ccggaggtaa                                     450
```

<210> SEQ ID NO 13
<211> LENGTH: 474
<212> TYPE: DNA
<213> ORGANISM: Artificial
<220> FEATURE:
<223> OTHER INFORMATION: Sequence encoding Chimeric VEGF protein

<400> SEQUENCE: 13

```
atgccggtca tgaggctgtt cccttgcttc ctgcagctcc tggccgggct ggcgctgcct     60
gctgtgcccc cccagcagtg ggccttgtct gctgggaacg gctcgtcaga ggtggaagtg    120
gtacccttcc aggaagtgtg gggccgcagc tactgccggg cgctggagag gctggtggac    180
gtcgtgtccg agtaccccag cgaggtggag cacatgttca gcccatcctg tgtctccctg    240
ctgcgctgca ccggctgctg cggcgatgag aatctgcact gtacagcggt tgaaacaaga    300
aatacaactg taacagtttc agtaaccggc gtgtctagtt cgtctggtac taatagtggt    360
gtatctacta accttcaaag aataagtgtt acagaacaca caaagtgcga atgccggcct    420
ctgcgggaga agatgaagcc ggaaaggtgc ggcgatgctg ttccccggag gtaa          474
```

<210> SEQ ID NO 14
<211> LENGTH: 474
<212> TYPE: DNA
<213> ORGANISM: Artificial
<220> FEATURE:
<223> OTHER INFORMATION: Sequence encoding Chimeric VEGF protein

<400> SEQUENCE: 14

```
atgccggtca tgaggctgtt cccttgcttc ctgcagctcc tggccgggct ggcgctgcct     60
gctgtgcccc cccagcagtg ggccttgtct gctgggaacg gctcgtcaga ggtggaagtg    120
gtacccttcc aggaagtgtg gggccgcagc tactgcaaac ctagagatac tgttgtttat    180
ttgggagaag aatatccaga aagcactaac ctacaatata atccccggtg tgtctccctg    240
ctgcgctgca ccggctgctg cggcgatgag aatctgcact gtacagcggt tgaaacaaga    300
aatacaactg taacagtttc agtaaccggc gtgtctagtt cgtctggtac taatagtggt    360
gtatctacta accttcaaag aataagtgtt acagaacaca caaagtgcga atgccggcct    420
ctgcgggaga agatgaagcc ggaaaggtgc ggcgatgctg ttccccggag gtaa          474
```

<210> SEQ ID NO 15
<211> LENGTH: 163
<212> TYPE: PRT
<213> ORGANISM: Artificial
<220> FEATURE:
<223> OTHER INFORMATION: Chimeric VEGF protein -continued

```
<400> SEQUENCE: 15

Met Pro Val Met Arg Leu Phe Pro Cys Phe Leu Gln Leu Leu Ala Gly
1               5                   10                  15

Leu Ala Leu Pro Ala Val Pro Pro Gln Gln Trp Ala Leu Ser Ala Gly
            20                  25                  30

Asn Gly Ser Ser Glu Val Glu Val Val Pro Phe Gln Glu Val Trp Gly
        35                  40                  45

Arg Ser Tyr Cys Lys Pro Arg Asp Thr Val Val Tyr Leu Gly Glu Glu
    50                  55                  60

Tyr Pro Glu Ser Thr Asn Leu Gln Tyr Asn Pro Arg Cys Val Ser Leu
65                  70                  75                  80

Leu Arg Cys Thr Gly Cys Cys Gly Asp Glu Asn Leu His Cys Thr Ala
                85                  90                  95

Val Glu Thr Arg Asn Thr Thr Val Thr Val Ser Val Thr Gly Val Ser
            100                 105                 110

Ser Ser Ser Gly Thr Asn Ser Gly Val Ser Thr Asn Leu Gln Arg Ile
        115                 120                 125

Ser Val Thr Glu His Thr Lys Cys Glu Cys Arg Pro Leu Arg Glu Lys
    130                 135                 140

Met Lys Pro Glu Arg Cys Gly Asp Ala Val Pro Arg Arg His His His
145                 150                 155                 160

His His His
```